(12) United States Patent
Barrow et al.

(10) Patent No.: US 12,611,399 B2
(45) Date of Patent: Apr. 28, 2026

(54) MOVEMENT DISORDERS

(71) Applicant: Definium Therapeutics US, Inc., New York, NY (US)

(72) Inventors: Robert Barrow, Madison, WI (US); Daniel R. Karlin, New York, NY (US)

(73) Assignee: Definium Therapeutics US, Inc., New York, NY (US)

( * ) Notice: Subject to any disclaimer, the term of this patent is extended or adjusted under 35 U.S.C. 154(b) by 0 days.

(21) Appl. No.: 17/734,102

(22) Filed: May 1, 2022

(65) Prior Publication Data

US 2022/0354831 A1 Nov. 10, 2022

Related U.S. Application Data

(60) Provisional application No. 63/183,771, filed on May 4, 2021.

(51) Int. Cl.
| | |
|---|---|
| *A61K 31/437* | (2006.01) |
| *A61K 31/4045* | (2006.01) |
| *A61K 45/06* | (2006.01) |
| *A61P 25/14* | (2006.01) |

(52) U.S. Cl.
CPC ........ *A61K 31/437* (2013.01); *A61K 31/4045* (2013.01); *A61K 45/06* (2013.01); *A61P 25/14* (2018.01)

(58) Field of Classification Search
CPC ...................................................... A61P 25/14
See application file for complete search history.

(56) References Cited

U.S. PATENT DOCUMENTS

| | | | |
|---|---|---|---|
| 1,394,233 | A | 10/1921 | Stoll |
| 2,090,429 | A | 8/1937 | Stoll et al. |
| 2,090,430 | A | 8/1937 | Stoll et al. |
| 2,265,207 | A | 12/1941 | Stoll et al. |
| 2,438,259 | A | 3/1948 | Stroll et al. |
| 2,447,214 | A | 8/1948 | Stoll et al. |
| 2,736,728 | A | 2/1956 | Pioch |
| 2,774,763 | A | 12/1956 | William |
| 2,796,419 | A | 6/1957 | Kornfeld et al. |
| 2,809,920 | A | 10/1957 | Arthur et al. |
| 2,997,470 | A | 8/1961 | Pioch |

(Continued)

FOREIGN PATENT DOCUMENTS

| | | |
|---|---|---|
| EP | 0816364 A1 | 1/1998 |
| EP | 1148339 A2 | 10/2001 |

(Continued)

OTHER PUBLICATIONS

Szabo et al., Psychedelic N, N-Dimethyltryptamine and 5-Methoxy-N, N-Dimethyltryptamine Modulate Innate and Adaptive Inflammatory Responses through the Sigma-1 Receptor of Human Monocyte-Derived Dendritic Cells, PLOS One, 2014, 9(8), pp. 1-12 (Year: 2014).*

(Continued)

*Primary Examiner* — Savitha M Rao
*Assistant Examiner* — Andrew P Lee
(74) *Attorney, Agent, or Firm* — COOLEY LLP

(57) ABSTRACT

A method of treating movement disorders, by administering an effective amount of a psychedelic to an individual having a movement disorder, and treating the movement disorder.

7 Claims, 2 Drawing Sheets

(56) References Cited

U.S. PATENT DOCUMENTS

| | | | |
|---|---|---|---|
| 3,038,840 | A | 6/1962 | Boris et al. |
| 3,085,092 | A | 4/1963 | Hofmann et al. |
| 3,239,530 | A | 3/1966 | Albert et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,925,678 | A | 5/1990 | Ranney |
| 4,959,217 | A | 9/1990 | Sanders et al. |
| 5,167,616 | A | 12/1992 | Haak et al. |
| 5,169,383 | A | 12/1992 | Gyory et al. |
| 5,225,182 | A | 7/1993 | Sharma |
| 6,063,908 | A | 5/2000 | Salamone et al. |
| 6,476,199 | B1 | 11/2002 | Salamone et al. |
| 6,794,496 | B2 | 9/2004 | Ghoshal et al. |
| 7,157,560 | B2 | 1/2007 | Ghoshal et al. |
| 7,566,549 | B2 | 7/2009 | Ghoshal et al. |
| 11,364,221 | B2 | 6/2022 | Liechti |
| 11,697,651 | B2 | 7/2023 | Muratore et al. |
| 11,717,517 | B2 | 8/2023 | Liechti et al. |
| 11,896,670 | B2 | 2/2024 | Trachsel et al. |
| 11,958,821 | B2 | 4/2024 | Clark |
| 11,959,929 | B2 | 4/2024 | Liechti et al. |
| 11,963,946 | B2 | 4/2024 | Liechti |
| 11,993,577 | B2 | 5/2024 | Fawaz et al. |
| 12,036,220 | B2 | 7/2024 | Mack et al. |
| 12,521,385 | B2 | 1/2026 | Mack et al. |
| 2001/0044118 | A1 | 11/2001 | Ghoshal et al. |
| 2003/0143655 | A1 | 7/2003 | McConnell et al. |
| 2006/0223998 | A1 | 10/2006 | Zhang et al. |
| 2007/0027208 | A1 | 2/2007 | Caron et al. |
| 2013/0287705 | A1 | 10/2013 | Khan et al. |
| 2018/0036303 | A1 | 2/2018 | Raz |
| 2018/0055791 | A1 | 3/2018 | Nichols et al. |
| 2019/0350949 | A1 | 11/2019 | Küçüksen et al. |
| 2020/0048205 | A1 | 2/2020 | Xiong et al. |
| 2020/0085816 | A1 | 3/2020 | Raz |
| 2020/0222656 | A1 | 7/2020 | Rustick |
| 2020/0323795 | A1 | 10/2020 | Glue et al. |
| 2020/0397752 | A1* | 12/2020 | Perez Castillo ....... A61K 45/06 |
| 2021/0085671 | A1 | 3/2021 | Chadeayne |
| 2021/0267977 | A1 | 9/2021 | Liechti |
| 2021/0315884 | A1 | 10/2021 | Liechti et al. |
| 2021/0346341 | A1 | 11/2021 | Liechti |
| 2021/0386704 | A1 | 12/2021 | Liechti et al. |
| 2022/0024956 | A1 | 1/2022 | Slassi et al. |
| 2022/0096429 | A1 | 3/2022 | Liechti |
| 2022/0128580 | A1 | 4/2022 | Liechti et al. |
| 2022/0143051 | A1 | 5/2022 | Manfredi et al. |
| 2022/0151986 | A1 | 5/2022 | Liechti et al. |
| 2022/0273628 | A1 | 9/2022 | Liechti et al. |
| 2022/0273644 | A1 | 9/2022 | Ribeiro et al. |
| 2022/0280501 | A1 | 9/2022 | Liechti et al. |
| 2022/0323405 | A1 | 10/2022 | Liechti |
| 2022/0347169 | A1 | 11/2022 | Liechti et al. |
| 2022/0347195 | A1 | 11/2022 | Barrow et al. |
| 2022/0348575 | A1 | 11/2022 | Levy et al. |
| 2022/0354822 | A1 | 11/2022 | Barrow et al. |
| 2022/0362237 | A1 | 11/2022 | Barrow et al. |
| 2022/0395499 | A1 | 12/2022 | Karlin et al. |
| 2023/0026731 | A1 | 1/2023 | Kochinke et al. |
| 2023/0039395 | A1 | 2/2023 | Liechti et al. |
| 2023/0059204 | A1 | 2/2023 | Plakogiannis et al. |
| 2023/0064429 | A1 | 3/2023 | Mack et al. |
| 2023/0066171 | A1 | 3/2023 | Trachsel et al. |
| 2023/0075847 | A1 | 3/2023 | Mack et al. |
| 2023/0088860 | A1 | 3/2023 | Muratore et al. |
| 2023/0096116 | A1 | 3/2023 | Fawaz et al. |
| 2023/0097530 | A1 | 3/2023 | Short et al. |
| 2023/0107398 | A1 | 4/2023 | Mack et al. |
| 2023/0116703 | A1 | 4/2023 | Kruegel |
| 2023/0122949 | A1 | 4/2023 | Mack et al. |
| 2023/0201160 | A1 | 6/2023 | Liechti |
| 2023/0210762 | A1 | 7/2023 | Ameri et al. |
| 2023/0218532 | A1 | 7/2023 | Mack et al. |
| 2023/0218568 | A1 | 7/2023 | Liechti |
| 2023/0219955 | A1 | 7/2023 | Sheshbaradaran et al. |
| 2023/0226019 | A1 | 7/2023 | Barrow et al. |
| 2023/0226020 | A1 | 7/2023 | Barrow et al. |
| 2023/0227420 | A1 | 7/2023 | Rao et al. |
| 2023/0227422 | A1 | 7/2023 | Duncton et al. |
| 2023/0233688 | A1 | 7/2023 | Liechti et al. |
| 2023/0248705 | A1 | 8/2023 | Gobbi et al. |
| 2023/0278977 | A1 | 9/2023 | Fawaz et al. |
| 2023/0285384 | A1 | 9/2023 | Liechti et al. |
| 2023/0285386 | A1 | 9/2023 | Mack et al. |
| 2023/0286975 | A1 | 9/2023 | Grill |
| 2023/0301985 | A1 | 9/2023 | Barrow et al. |
| 2023/0310368 | A1 | 10/2023 | Barrow et al. |
| 2023/0330085 | A1 | 10/2023 | Liechti et al. |
| 2023/0346645 | A1 | 11/2023 | Barrow et al. |
| 2023/0355575 | A1 | 11/2023 | Liechti et al. |
| 2023/0414583 | A1 | 12/2023 | Trachsel et al. |
| 2023/0416219 | A1 | 12/2023 | Schneider et al. |
| 2024/0010628 | A1 | 1/2024 | Schneider et al. |
| 2024/0041860 | A1 | 2/2024 | Dolen et al. |
| 2024/0115710 | A1 | 4/2024 | Trachsel et al. |
| 2024/0285576 | A1 | 8/2024 | Smagin |
| 2024/0285577 | A1 | 8/2024 | Nair et al. |
| 2025/0019359 | A1 | 1/2025 | Schneider et al. |
| 2025/0152565 | A1 | 5/2025 | Liechti et al. |
| 2025/0312309 | A1 | 10/2025 | Trachsel et al. |
| 2025/0345323 | A1 | 11/2025 | Mack et al. |

FOREIGN PATENT DOCUMENTS

| | | | | |
|---|---|---|---|---|
| FR | 1338023 | A | 9/1963 | |
| GB | 579484 | A | 8/1946 | |
| WO | WO-2006010587 | A1 | 2/2006 | |
| WO | WO-2006128658 | A1 | 12/2006 | |
| WO | WO-2014059197 | A1 | 4/2014 | |
| WO | 2019246532 | † | 12/2019 | |
| WO | WO-2020181194 | A1 | 9/2020 | |
| WO | 2020212948 | † | 10/2020 | |
| WO | 2020212951 | † | 10/2020 | |
| WO | WO-2020212952 | A1 * | 10/2020 | ......... A61K 31/4045 |
| WO | WO-2020232255 | A1 | 11/2020 | |
| WO | WO-2021019023 | A1 | 2/2021 | |
| WO | WO-2021173273 | A1 | 9/2021 | |
| WO | WO-2021211358 | A1 | 10/2021 | |
| WO | WO-2021225796 | A1 | 11/2021 | |
| WO | WO-2021243461 | A1 | 12/2021 | |
| WO | WO-2021257169 | A1 | 12/2021 | |
| WO | WO-2022008627 | A2 | 1/2022 | |
| WO | WO-2022023812 | A1 | 2/2022 | |
| WO | WO-2022023813 | A1 | 2/2022 | |
| WO | WO-2022084892 | A1 | 4/2022 | |
| WO | WO-2022106947 | A1 | 5/2022 | |
| WO | WO-2022107095 | A1 | 5/2022 | |
| WO | WO-2022150525 | A1 | 7/2022 | |
| WO | WO-2022175821 | A1 | 8/2022 | |
| WO | WO-2022189907 | A1 | 9/2022 | |
| WO | WO-2022214889 | A1 | 10/2022 | |
| WO | WO-2022221942 | A1 | 10/2022 | |
| WO | WO-2022226408 | A1 | 10/2022 | |
| WO | WO-2022232093 | A1 | 11/2022 | |
| WO | WO-2022235500 | A1 | 11/2022 | |
| WO | WO-2022235529 | A1 | 11/2022 | |
| WO | WO-2022235530 | A1 | 11/2022 | |
| WO | WO-2022235531 | A1 | 11/2022 | |
| WO | WO-2022261058 | A1 | 12/2022 | |
| WO | WO-2022265878 | A1 | 12/2022 | |
| WO | WO-2023283373 | A1 | 1/2023 | |
| WO | WO-2023283386 | A2 | 1/2023 | |
| WO | WO-2023012524 | A2 | 2/2023 | |
| WO | WO-2023023182 | A1 | 2/2023 | |
| WO | WO-2023023192 | A1 | 2/2023 | |
| WO | WO-2023028022 | A1 | 3/2023 | |
| WO | WO-2023043870 | A1 | 3/2023 | |
| WO | WO-2023092044 | A2 | 5/2023 | |
| WO | WO-2023107966 | A1 | 6/2023 | |
| WO | WO-2023108277 | A1 | 6/2023 | |

(56)　　　　　References Cited

FOREIGN PATENT DOCUMENTS

| WO | WO-2023114529 A2 | 6/2023 |
|---|---|---|
| WO | WO-2023115006 A1 | 6/2023 |
| WO | WO-2023131841 A1 | 7/2023 |
| WO | WO-2023183618 A1 | 9/2023 |
| WO | WO-2023212244 A1 | 11/2023 |
| WO | WO-2023250247 A2 | 12/2023 |
| WO | WO-2023250298 A1 | 12/2023 |
| WO | WO-2024011067 A2 | 1/2024 |
| WO | WO-2024033910 A1 | 2/2024 |
| WO | WO-2024054688 A2 | 3/2024 |
| WO | WO-2024091506 A2 | 5/2024 |
| WO | WO-2024123706 A1 | 6/2024 |
| WO | WO-2024182074 A1 | 9/2024 |
| WO | WO-2024196772 A2 | 9/2024 |
| WO | WO-2024206000 A2 | 10/2024 |
| WO | WO-2024229454 A2 | 11/2024 |
| WO | WO-2024238035 A1 | 11/2024 |
| WO | WO-2024253775 A1 | 12/2024 |
| WO | WO-2024263978 A1 | 12/2024 |
| WO | WO-2025128594 A1 | 6/2025 |

OTHER PUBLICATIONS

Nguyen et al., Role of sigma-1 receptors in neurodegenerative diseases, Journal of Pharmacological Sciences, 2015, 127, pp. 17-29 (Year: 2015).*
Szabo et al., Psychedelics and immunomodulation: novel approaches and therapeutic opportunities, Frontiers in Immunology, 2015 , 6(358), pp. 1-11 (Year: 2015).*
Butler et al., Psychedelic treatment of functional neurological disorder: a systematic review, Therapeutic Advances in Psychopharmacology, 2020, 10, pp. 1-15 (Year: 2020).*
Brammer et al., Interactions between 3,4-ethylenedioxymethamphetamine and σ1 receptors, European Journal of Pharmacology, 2006, pp. 141-145 (Year: 2006).*
Logigian, Does Tremor Pace Repetitive Voluntary Motor Behavior in Parkinson's Disease?, Annals of Neurology, 1991, 30(2), pp. 172-179 (Year: 1991).*
Lopez-Sendon et al., Drug-induced parkinsonism, Expert Opinion on Drug Safety, 2013, 4, pp. 487-496 (Year: 2013).*
Pitts et al., (±)-MDMA and its enantiomers: potential therapeutic advantages of R(−)-MDMA, Psychopharmacology, 2018, 235, pp. 377-392 (Year: 2018).*
Adams et al., "Patterns of exploration in rats distinguish lisuride from lysergic acid diethylamide." Pharmacology Biochemistry and Behavior (1985); 23(3): 461-468. doi: 10.1016/0091-3057(85)90022-x.
Aghajanian et al., "Serotonin and Hallucinogens." Neuropsychopharmacology (1999); 21(2):16S-23S. doi: 10.1016/S0893-133X(98)00135-3.
Aghajanian et al., "Serotonin Induces Excitatory Postsynaptic Potentials in Apical Dendrites of Neocortical Pyramidal Cells", Neuropharmacology (1997); 36(4-5): 589-599. doi: 10.1016/s0028-3908(97)00051-8.
Aghajanian et al., "Persistence of lysergic acid diethylamide in the plasma of human subjects", Clinical Pharmacology & Therapeutics (1964); 5: 611-614. doi: 10.1002/cpt196455611.
Alaka et al., "Efficacy and safety of duloxetine in the treatment of older adult patients with generalized anxiety disorder: a randomized, double-blind, placebo-controlled trial", International Journal of Geriatric Psychiatry (2014); 29(9): 978-986. doi: 10.1002/gps.4088. Epub Feb. 20, 2014.
Alexander et al., "LSD: Injection early in pregnancy produces abnormalities in offspring in rats", Science (1967); 157: 459-460. doi: 10.1126/science.157.3787.459.
Alexander et al., "Lysergic acid diethylamide intake in pregnancy: Fetal damage in rats", The Journal of Pharmacology and Experimental Therapeutics (1970); 173: 48-59.

Allgulander et al., "Efficacy of sertraline in a 12-week trial for generalized anxiety disorder", American Journal of Psychiatry (Sep. 2004); 161(9): 1642-1649. doi: 10.1176/appi.ajp.161.9.1642.
Anderson et al., "Absolute configuration and psychotomimetic activity", 'QuaSAR' Research Monograph, National Institute on Drug Abuse (1978); 22: 8-15.
Ansara. "Management of treatment-resistant generalized anxiety disorder", Mental Health Clinician (2020); 10(6): 326-334. doi: 10.9740/mhc.2020.11.326.
Ansseau et al., "Controlled comparison of tianeptine, alprazolam and mianserin in the treatment of adjustment disorders with anxiety and depression", Human Psychopharmacology Clinical and Experimental (1996); 11(4): 293-298.
Antkiewicz-Michaluk et al., "Ca2+ channel blockade prevents lysergic acid diethylamine-induced changes in dopamine and serotonin metabolism", European Journal of Pharmacology (1997); 332(1): 9-14. doi: 10.1016/s0014-2999(97)01025-x.
Appel et al., "Analyzing mechanism(s) of hallucinogenic drug action with drug discrimination procedures", Neuroscience & Biobehavioral Reviews (1982); 6(4): 529-536. doi: 10.1016/0149-7634(82)90036-7.
Appel et al., "LSD, 5-HT (serotonin), and the evolution of a behavioral assay", Neuroscience and Biobehavioral Reviews (2004); 27(8): 693-701. doi: 10.1016/j.neubiorev.2003.11.012.
Auerbach et al., "Lysergic acid diethylamine: effect on embryos", Science (1967); 157: 1325-1326. doi: 10.1126/science.157.3794.1325.
Axelrod et al., "The distribution and metabolism of lysergic acid diethylamide." Annals New York Academy of Sciences, 1957; 66(3): 435-444. doi: 10.1111/j.1749-6632.1957.tb40739.x.
Babor et al., "The Alcohol Use Disorders Identification Test, Guidelines for Use in Primary Care, Second Edition", World Health Organization, Department of Mental Health and Substance Dependence (2001) [online] https://apps.who.int/iris/bitstream/handle/10665/67205/WHO_MSD_MSB_01.6a.pdf?sequence=1&isAllowed=y (Access Date: Nov. 1, 2021); 41 pages.
Bailey et al., "Distinction of Some Dialkyl Amides of Lysergic and iso-Lysergic Acids from LSD", Journal of the Association of Official Analytical Chemists (1973); 56(1): 88-99.
Baker et al., "Molecular structure of LSD", Science (1972); 178(4061): 614-615. doi: 10.1126/science.178.4061.614.
Bandelow et al., "Epidemiology of anxiety disorders in the 21st century", Dialogues in Clinical Neuroscience (2015); 17(3): 327-335. doi: 10.31887/DCNS.2015.17.3/bbandelow.
Barnett. "Diazepam treatment for L.S.D. intoxication", Lancet (1971); 2: 270; 1 page. doi: 10.1016/s0140-6736(71)92616-x.
Barrett et al., "Serotonin 2A receptor signaling underlies LSD-induced alteration of the neural response to dynamic changes in music", Cerebral Cortex (2018); 28(11): 3939-3950. doi: 10.1093/cercor/bhx257.
Barrett et al., "Validation of the revised Mystical Experience Questionnaire in experimental sessions with psilocybin", Journal of Psychopharmacology (2015); 29(11): 1182-1190. doi: 10.1177/0269881115609019. Epub Oct. 6, 2015.
Baumeister et al., "Classical hallucinogens as antidepressants? A review of pharmacodynamics and putative clinical roles", Therapeutic Advances in Psychopharmacology (2014); 4(4): 156-169. doi: 10.1177/2045125314527985.
Bedard et al., "The 'wet dog shake' behaviour in the rat and 5 hydroxytryptamine", British Journal of Pharmacology (1977); 59(3): 450P-451P; 2 pages.
Ben-Jonathan et al., "What can we learn from rodents about prolactin in humans?", Endocrine Reviews (2008); 29(1): 1-41. doi: 10.1210/er.2007-0017. Epub Dec. 5, 2007.
Bercel et al., "Model Psychoses Induced by LSD-25 in Normals: I. Psychophysiological Investigations, with Special Reference to the Mechanism of the Paranoid Reaction", AMA Archives of Neurology and Psychiatry (1956); 75(6): 588-611. doi: 10.1001/archneurpsyc.1956.02330240026003.
Berman et al., "Evaluation of the Drug Use Disorders Identification Test (DUDIT) in criminal justice and detoxification settings and in a Swedish population sample", European Addiction Research (2005); 11(1): 22-31. doi: 10.1159/000081413.

(56)             References Cited

OTHER PUBLICATIONS

Bershad et al., "Acute Subjective and Behavioral Effects of Microdoses of Lysergic Acid Diethylamide in Healthy Human Volunteers", Biological Psychiatry (2019); 86(10): 792-800. doi.org/10.1016/j.biopsych.2019.05.019.

Bershad et al., "Preliminary report on the effects of a low dose of LSD on resting-state amygdala Functional connectivity", Biological Psychiatry: Cognitive Neuroscience and Neuroimaging (2020); 5(4): 461-467. doi: 10.1016/j.bpsc.2019.12.007. Epub Dec. 20, 2019.

Boess et al., "Interaction of tryptamine and ergoline compounds with threonine 196 in the ligand binding site of the 5-hydroxytryptamine6 receptor", Molecular Pharmacology (1997); 52: 515-523. doi: 10.1124/mol.52.3.515.

Boess et al., "Molecular biology of 5-HT receptors", Neuropharmacology (1994); 33(3/4): 275-317. doi: 10.1016/0028-3908(94)90059-0.

Bogenschutz et al., "Psilocybin-assisted treatment for alcohol dependence: a proof-of-concept study." Journal of Psychopharmacology (Mar. 2015); 29(3): 289-299. doi: 10.1177/0269881114565144. Epub Jan. 13, 2015.

Bonson et al., "Alterations in responses to LSD in humans associated with chronic administration of tricyclic antidepressants, monoamine oxidase inhibitors or lithium", Behavioural Brain Research (1996); 73(1-2): 229-233. doi: 10.1016/0166-4328(96)00102-7.

Bonson et al., "Chronic administration of serotonergic antidepressants attenuates the subjective effects of LSD in humans", Neuropsychopharmacology (1996); 14(6): 425-436. doi: 10.1016/0893-133X(95)00145-4.

Boyd et al., "Preliminary studies of the metabolism of lysergic acid diethylamide using radioactive carbon-marked molecules", Journal of Nervous and Mental Disease (1955); 122(5): 470-471. doi: 10.1097/00005053-195511000-00009.

Boyd. "Preliminary Studies on the Metabolism of LSD", In: Cholden, L. (ed), Proceedings of the Round Table on Lysergic Acid Diethylamide and Mescaline in Experimental Psychiatry, Grune & Stratton, New York and London (1956); 57-59; 5 pages.

Boyd. "The metabolism of lysergic acid diethylamide", Archives Internationales de Pharmacodynamie et de Therapie (Jul. 1959); 120: 292-311.

Brandt et al., "Return of the lysergamides. Part II: analytical and behavioural characterization of N6-allyl-6-norlysergic acid diethylamide (AL-LAD) and (2'S, 4'S)-lysergic acid 2, 4-dimethylazetidide (LSZ)", Drug Testing and Analysis (2017); 9(1): 38-50. doi: 10.1002/dta.1985. Epub Jun. 6, 2016.

Brandt et al., "Return of the lysergamides. Part VI: Analytical and behavioural characterization of 1-cyclopropanoyl-d-lysergic acid diethylamide (1CP-LSD)", Drug Testing and Analysis (2020); 12(6): 812-826. doi: 10.1002/dta.2789. Epub Apr. 20, 2020.

Bretz et al., "Combining multiple comparisons and modeling techniques in dose-response studies", Biometrics (2005); 61(3): 738-748. doi: 10.1111/j.1541-0420.2005.00344.x.

Bruss et al., "Hamilton anxiety rating scale interview guide: Joint interview and test-retest methods for interrater reliability", Psychiatry Research (1994); 53: 191-202. doi: 10.1016/0165-1781(94)90110-4.

Buchborn et al., "Tolerance to lysergic acid diethylamide: Overview, correlates, and clinical implications." Neuropathology of Drug Addictions and Substance Misabuse, vol. 2, Chapter 79 (2016): 846-858.

Bunzow et al., "Amphetamine, 3,4-methylenedioxymethamphetamine, lysergic acid diethylamide, and metabolites of the catecholamine neurotransmitters are Agonists of a rat trace amine receptor", Molecular Pharmacology (2001); 60(6): 1181-1188. doi: 10.1124/mol.60.6.1181.

Butler, et al., "Psychedelic treatment of functional neurological disorder: a systematic review", Therapeutic Advances in Psychopharmacology (2020); 10: 1-15. doi: 10.1177/2045125320912125.

Buysse et al., "The Pittsburgh Sleep Quality Index: a new instrument for psychiatric practice and research", Psychiatry Research (1989); 28(2): 193-213. doi: 10.1016/0165-1781(89)90047-4.

Cai et al., "Elucidation of LSD in vitro metabolism by liquid chromatography and capillary electrophoresis coupled with tandem mass spectrometry", The Journal of Analytical Toxicology (Jan./Feb. 1996); 20: 27-37. doi: 10.1093/jat/20.1.27.

Canezin et al., "Determination of LSD and its metabolites in human biological fluids by high-performance liquid chromatography with electrospray tandem mass spectrometry", Journal of Chromatography B (2001); 765(1): 15-27. doi: 10.1016/s0378-4347(01)00386-3.

Cao et al., "Structure-based discovery of nonhallucinogenic psychedelic analogs", Science (2022); 375(6579): 403-411. doi: 10.1126/science.abl8615. Epub Jan. 27, 2022.

Carhart-Harris et al., "LSD enhances suggestibility in healthy volunteers", Psychopharmacology (Berl) (Feb. 2015); 232(4): 785-794. doi: 10.1007/s00213-014-3714-z. Epub Sep. 23, 2014.

Carhart-Harris et al., "Psilocybin with psychological support for treatment-resistant depression: six-month follow-up", Psychopharmacology (2018); 235: 399-408. doi: 10.1007/s00213-017-4771-x. Epub Nov. 8, 2017.

Carhart-Harris et al., "The paradoxical psychological effects of lysergic acid diethylamide (LSD)", Psychological Medicine (2016); 46(7): 1379-1390. doi: 10.1017/S0033291715002901. Epub Feb. 5, 2016.

Cerny et al., "Mutterkornalkaloide XIX. Über die Verwendung von N, N'- Carbonyldiimidazol zur Synthese der D-Lysergsäure-, D-Dihydrolysergsäure (I)-und 1-Methyl-D-dihydrolysergsaure (I) amide", Collection of Czechoslovak Chemical Communications (1962); 27(7): 1585-1592; 17 pages with English machine translation.

Chen et al., "Anxiety in Parkinson's disease: identification and management", Therapeutic Advances in Neurological Disorders (Jan. 2014); 7(1): 52-59. doi: 10.1177/1756285613495723.

Cohen et al., "Chromosomal Damage in Human Leukocytes Induced by Lysergic Acid Diethylamide", Science (1967); 155(3768): 1417-1419. doi: 10.1126/science.155.3768.1417.

Cohen et al., "Genetic toxicology of lysergic acid diethylamide (LSD-25)", Mutation Research/Reviews in Genetic Toxicology (1977); 47(3-4): 183-209. doi: 10.1016/0165-1110(77)90003-3.

Cohen et al., "In vivo and in vitro chromosomal damage induced by LSD-25", New England Journal of Medicine (Nov. 16, 1967); 277(20): 1043-1049. doi: 10.1056/NEJM196711162772001.

Cohen et al., "Meiotic chromosome damage induced by LSD-25", Nature (1968); 219: 1072-1074. doi: 10.1038/2191072a0.

Collu et al., "Endocrine effects of chronic administration of psychoactive drugs to prepubertal male rats. II LSD", Canadian Journal of Physiology and Pharmacology (1975); 53(6): 1023-1026. doi: 10.1139/y75-142.

Constantin et al., "Therapeutic Interventions for Adjustment Disorder: A Systematic Review", American Journal of Therapeutics (2020); 27(4): e375-e386.

Corey et al., "Chromosome studies on the patients (in vivo) and cells (in vitro) treated with lysergic acid diethylamide", New England Journal of Medicine (1970); 282(17): 939-943. doi: 10.1056/NEJM197004232821702.

Corne et al., "A possible correlation between drug-induced hallucinations in man and a behavioural response in mice", Psychopharmacologia (Berl.) (1967); 11: 65-78. doi: 10.1007/BF00401509.

Creese et al., "The dopamine receptor: differential binding of d-LSD and related agents to agonist and antagonist states", Life Sciences (1975); 17(11): 1715-1719. doi: 10.1016/0024-3205(75)90118-6.

Danforth. "Embracing neurodiversity in psychedelic science: A mixed-methods inquiry into the MDMA experiences of autistic adults", Journal of Psychoactive Drugs (2019); 51(2): 146-154. doi: 10.1080/02791072.2019.1587116. Epub Mar. 25, 2019.

Darke et al., "A retrospective study of the characteristics and toxicology of cases of lysergic acid diethylamide (LSD)-and psilocybin-related death in Australia", Addiction, (2024); 119: 1564-1571. doi: 10.1111/add.16518. Epub May 21, 2024.

Database Stn, CAS Registry No. 2757566-19-9, "Ergoline-8-carboxamide, 9,10-didehydro-N-ethyl-N-(2-fluoroethyl)-6-methyl-, (8β)-" [CA Index Name]. Chemical Abstracts Service, American Chemical Society; entered Jan. 28, 2022; 1 printed page.

(56)          References Cited

OTHER PUBLICATIONS

Database STN, CAS Registry No. 2855122-73-3, "Ergoline-8-carboxamide, 9,10-didehydro-N,N-bis(2-fluoroethyl)-6-methyl-, (8β)-" [CA Index Name]. Chemical Abstracts Service, American Chemical Society; entered Nov. 17, 2022; 1 printed page.

Database STN, CAS Registry No. 2855123-59-8, "Ergoline-8-carboxamide, 9,10-didehydro-N,N-bis(2-fluoroethyl)-6-methyl-, (8β)-" [CA Index Name]. Chemical Abstracts Service, American Chemical Society; entered Nov. 17, 2022; 1 printed page.

Database STN, CAS Registry No. 3024529-93-6, "Ergoline-8-carboxamide, 9,10-didehydro-N-ethyl-N-2-propyn-1-yl-6-methyl-,(8β)-" [CA Index Name]. Chemical Abstracts Service, American Chemical Society; entered Jan. 11, 2024; 1 printed page.

Database STN, CAS Registry No. 3024530-02-4, "Ergoline-8-carboxamide, 9,10-didehydro-N-ethyl-N-methoxy-6-methyl-,(8β)-" [CA Index Name]. Chemical Abstracts Service, American Chemical Society; entered Jan. 11, 2024; 1 printed page.

Database STN, CAS Registry No. 3024530-08-0, "Ergoline-8-carboxamide, 9,10-didehydro-N-(2-fluoroethyl)-N-methoxy-6-methyl-, (8β)-" [CA Index Name]. Chemical Abstracts Service, American Chemical Society; entered Jan. 11, 2024; 1 printed page.

Database STN, CAS Registry No. 3024530-10-4, "Ergoline-8-carboxamide, 9,10-didehydro-N,N-diethyl-6-(2-fluoro-2-propen-1-yl)-, (8β)-" [CA Index Name]. Chemical Abstracts Service, American Chemical Society; entered Jan. 11, 2024; 1 printed page.

Database STN, CAS Registry No. 3024530-16-0, "Ergoline-8-carboxamide, 9,10-didehydro-N, N-diethyl-6-(2-oxopropyl)-, (8β)-" [CA Index Name]. Chemical Abstracts Service, American Chemical Society; entered Jan. 11, 2024; 1 printed page.

Database STN, CAS Registry No. 3024530-28-4, "Ergoline-8-carboxamide, 9,10-didehydro-N, N-diethyl-6-(2-fluoroethyl)-, (8β)-" [CA Index Name]. Chemical Abstracts Service, American Chemical Society; entered Jan. 11, 2024; 1 printed page.

Database STN, CAS Registry No. 3024530-30-8, "Ergoline-8-carboxamide, 9,10-didehydro-N-ethyl-6-(2-fluoro-2-propen-1-yl)-N-2-propyn-1-yl-, (8β)-" [CA Index Name]. Chemical Abstracts Service, American Chemical Society; entered Jan. 11, 2024; 1 printed page.

Database STN, CAS Registry No. 65527-59-5, "Ergoline-8-carboxamide, 9,10-didehydro-N-ethenyl-N-ethyl-6-methyl-, (8β)-(9CI)" [Ca Index Name]. Chemical Abstracts Service, American Chemical Society; entered Nov. 16, 1984; 1 printed page.

Davenport. "Psychedelic and nonpsychedelic LSD and psilocybin for cluster headache", CMAJ (2016); 188(3): 217; 1 page. doi: 10.1503/cmaj.1150082.

De Gregorio et al., "d-Lysergic Acid Diethylamide (LSD) as a Model of Psychosis: Mechanism of Action and Pharmacology", International Journal of Molecular Science, (2016); 17(11): 1953; 20 pages. doi: 10.3390/ijms17111953.

De Gregorio et al., "The hallucinogen d-lysergic diethylamide (LSD) decreases dopamine firing activity through 5-HT1A, D2 and TAAR1 receptors", Pharmacological Research (2016); 113: 81-91. doi: 10.1016/j.phrs.2016.08.022. Epub Aug. 17, 2016.

Dipaolo et al., "Evaluation of teratogenicity of lysergic acid diethylamine", Nature (1968); 220: 490-491. doi: 10.1038/220490b0.

Dirami et al., "Effect of a dopamine agonist on the development of Leydig Cell hyperplasia in Sprague-Dawley rats", Toxicology and Applied Pharmacology (1996); 141: 169-177. doi: 10.1006/taap.1996.0273.

Dishotsky et al., "LSD and genetic damage: Is LSD chromosome damaging, carcinogenic, mutagenic, or teratogenic?", Science (1971); 172(3982): 431-440. doi: 10.1126/science.172.3982.431.

Dittrich. "The standardized psychometric assessment of altered states of consciousness (ASCs) in humans", Pharmacopsychiatry (1998); 31(Suppl 2): 80-84. doi: 10.1055/s-2007-979351.

Dolder et al., "Development and validation of a rapid turboflow LC-MS/MS method for the quantification of LSD and 2-oxo-3-hydroxy LSD in serum and urine samples of emergency toxicological cases", Analytical and Bioanalytical Chemistry (2015); 407: 1577-1584. doi.10.1007/s00216-014-8388-1.

Dolder et al., "Development and validation of an LC-MS/MS method to quantify lysergic acid diethylamide (LSD), iso-LSD, 2-oxo-3-hydroxy-LSD, and nor-LSD and identify novel metabolites in plasma samples in a controlled clinical trial", Journal of Clinical Lab Analysis (2018); 32(2): 1-8. doi: 10.1002/jcla.22265. Epub May 26, 2017.

Dolder et al., "LSD acutely impairs fear recognition and enhances emotional empathy and sociality", Neuropsychopharmacology (2016); 41(11): 2638-2646. doi: 10.1038/npp.2016.82. Epub Jun. 1, 2016.

Dolder et al., "Pharmacokinetics and pharmacodynamics of lysergic acid diethylamide in healthy subjects", Clinical Pharmacokinetics (2017); 56: 1219-1230. doi: 10.1007/s40262-017-0513-9.

Dolder et al., "Pharmacokinetics and concentration-effect relationship of oral LSD in humans." International Journal of Neuropsychopharmacology (2016); 19(1): pyv072; 7 pages. doi: 10.1093/ijnp/pyv072. Erratum in: Int J Neuropsychopharmacol. Apr. 27, 2016;19(10):pyw031. doi: 10.1093/ijnp/pyw031. P.

Duerler et al., "LSD-induced increases in social adaptation to opinions similar to one's own are associated with stimulation of serotonin receptors", Scientific Reports (2020); 10: 12181; 11 pages. doi: 10.1038/s41598-020-68899-y.

Eells et al., "Effects of intraocular mescaline and LSD on visual-evoked responses in the rat", Pharmacology Biochemistry & Behavior (1989); 32: 191-196. doi: 10.1016/0091-3057(89)90232-3.

Effenberger et al., "Stereoselective Synthesis of (S)-3, 4-Methylenedioxyamphetamines from (R)-Cyanohydrins", Chemistry—A European Journal (1997); 3(8): 1370-1374.

Egan et al., "Agonist activity of LSD and lisuride at cloned 5-HT2A and 5-HT2C receptors", Psychopharmacology (1998); 136: 409-414. doi: 10.1007/s002130050585.

Eglen et al., "The 5-HT7 receptor: orphan found", Trends in Pharmacological Sciences (Apr. 1997); 18(4): 104-107. doi: 10.1016/s0165-6147(97)01043-2.

Egozcue et al., "Effect of LSD-25 on mitotic and meiotic chromosomes of mice and monkeys", Humangenetik (1969); 8: 86-93. doi: 10.1007/BF00295831.

Eleusis Therapeutics, "A Double-blind, Placebo-controlled Study to Evaluate Very Low Dose LSD in Healthy Volunteers Aged 55-75 Years" ClinicalTrials.gov ID NCT04421105, version 1, Jun. 4, 2020, 12 pages.

EMCDDA (European Monitoring Center for Drugs and Drug Addiction). "Statistical Bulletin 2021—prevalence of drug use." [online] https://www.emcdda.europa.eu/data/stats2021/gps_en (Access Date: Nov. 1, 2021); 1 page.

Emerit et al., "LSD: No chromosomal breakage in mother embryos during rat pregnancy", Teratology (1972); 6: 71-74. doi: 10.1002/tera.1420060109.

Erickson et al., "Severity of anxiety and work-related outcomes of patients with anxiety disorders", Depress and Anxiety (2009); 26(12): 1165-1171. doi: 10.1002/da.20624.

Erowid. "1P-LSD Reports (also 1-propionyl-lysergic acid diethyl-amide) (125 Total)", The Erowid Experience Vaults [online] https://erowid.org/experiences/subs/exp_1PLSD.shtml (Access Date: Mar. 14, 2025); 4 pages.

Erpelding et al., "Placebo Response Reduction and Accurate Pain Reporting Training Reduces Placebo Responses in a Clinical Trial on Chronic Low Back Pain", Clinical Journal Pain (2020); 36(12): 950-954. doi: 10.1097/AJP.0000000000000873.

Evans et al., "What can be done to control the placebo response in clinical trials? A narrative review", Contemporary Clinical Trials (2021); 107: 106503; 8 pages. doi: 10.1016/j.cct.2021.106503. Epub Jul. 6, 2021.

Evarts. "Some effects of bufotenine and lysergic acid diethylamide on the monkey", AMA Archives of Neurology and Psychiatry (1956); 75(1): 49-53. doi: 10.1001/archneurpsyc.1956.02330190065004.

Examiner Interview Summary for U.S. Appl. No. 17/734, 102, by Barrow, Robert, et al., mailed on Sep. 11, 2023, 2 pages.

Family et al., "Safety, tolerability, pharmacokinetics, and pharmacodynamics of low dose lysergic acid diethylamide (LSD) in

(56) References Cited

OTHER PUBLICATIONS healthy older volunteers", Psychopharmacology (2020); 237: 841-853. doi: 10.1007/s00213-019-05417-7. Epub Dec. 18, 2019.

Fava et al., "Major Depressive Disorder", Neuron (2000); 28: 335-341. doi: 10.1016/s0896-6273(00)00112-4.

Felix Mueller, "LSD Treatment for Persons With Alcohol Use Disorder (LYSTA)" ClinicalTrials.gov Id NCT05474989, version 1, Jul. 24, 2022, 11 pages.

Fiorella et al., "The role of the 5-HT2A and 5-HT2C receptors in the stimulus effects of hallucinogenic drugs III: The mechanistic basis for supersensitivity to the LSD stimulus following serotonin depletion", Psychopharmacology (1995); 121: 364- 372. doi: 10.1007/BF02246076.

Ford et al., "Hallucinogenic Persisting Perception Disorder: A case series and review of the literature" Frontiers in Neurology, May 2022; 13: 878609; 10 pages. doi: 10.3389/fneur.2022.878609.

Frank et al., "Efficacy of interpersonal psychotherapy as a maintenance treatment of recurrent depression", Archives of General Psychiatry (1991); 48: 1053-1059. doi: 10.1001/archpsyc.1991.01810360017002.

Freedman et al., "266-Regional and subcellular distribution of LSD and effects on 5-HT levels", The Pharmacologist, Neurochemistry, Abstracts of Papers for Fall Meeting (Aug. 16-20, 1965); 7(2); 3 pages.

Freedman et al., "Patterns of tolerance to lysergic acid diethylamide and mescaline in rats", Science (1958); 127: 1173-1174. doi: 10.1126/science.127.3307.1173.

Freedman et al., "Tolerance to behavioral effects of LSD-25 in the rat", Journal of Pharmacology and Experimental Therapeutics (1964); 143: 309-313.

Freedman. "The Psychopharmacology of Hallucinogenic Agents", Annual Review Medicine (1969); 20(1): 409-418. doi: 10.1146/annurev.me.20.020169.002205.

Fuentes et al., "Therapeutic use of LSD in psychiatry: A systematic review of randomized-controlled clinical trials", Front Psychiatry (2020); 10: 943; 14 pages. doi: 10.3389/fpsyt.2019.00943.

Galanopoulou et al., "Mesulergine: A review", CNS Drug Reviews (1999); 5(3): 233-248.

Garakani et al., "Pharmacology of anxiety disorders: Current and emerging treatment options", Frontiers in Psychiatry (Dec. 2020); 11(595584); 21 pages. doi: 10.3389/fpsyt.2020.595584.

Garbrecht. "Synthesis of Amides of Lysergic Acid1", The Journal of Organic Chemistry (1959); 24(3): 368-372.

Gartlehner et al., "Comparative benefits and harms of second-generation antidepressants for treating major depressive disorder: An updated meta-analysis", Annals of Internal Medicine (2011); 155(11): 772-785. doi: 10.7326/0003-4819-155-11-201112060-00009.

Gasser et al., "Safety and efficacy of lysergic acid diethylamide-assisted psychotherapy for anxiety associated with life-threatening diseases", Journal of Nervous and Mental Disease (2014); 202(7): 513-520. doi: 10.1097/NMD.0000000000000113.

Gasser et al., "LSD-assisted psychotherapy for anxiety associated with a life-threatening disease: a qualitative study of acute and sustained subjective effects", Journal of Psychopharmacology (2015); 29(1): 57-68. doi: 10.1177/0269881114555249. Epub Nov. 11, 2014.

Geber. "Congenital malformations induced by mescaline, lysergic acid diethylamide and bromolysergic acid in the hamster", Science (1967); 158: 265-267. doi: 10.1126/science.158.3798.265.

Gerald et al., "The 5-HT4 receptor: Molecular cloning and pharmacological characterization of two splice variants", EMBO Journal (1995); 14(12): 2806-2815. doi: 10.1002/j.1460-2075.1995.tb07280.x.

Giacomelli et al., "Lysergic acid diethylamide (LSD) is a partial agonist of D2 dopaminergic receptors and it potentiates dopamine-mediated prolactin secretion in lactotrophs in vitro", Life Sciences (1998); 63(3): 215-222. doi: 10.1016/s0024-3205(98)00262-8.

Goetz et al., "The mutagenic effect of lysergic acid diethylamine I. Cytogenetic analysis", Mutation Research (1974); 26: 513-516. doi: 10.1016/s0027-5107(74)80052-7.

Gonzalez-Maeso et al., "Transcriptome Fingerprints Distinguish Hallucinogenic and Nonhallucinogenic 5-Hydroxytryptamine 2A Receptor Agonist Effects in Mouse Somatosensory Cortex", The Journal of Neuroscience (2003); 23(26): 8836-8843. doi: 10.1523/JNEUROSCI.23-26-08836.2003.

Gonzalez-Martinez et al., "Stereoselective synthesis of 1-arylpropan-2-amines from allylbenzenes through a Wacker-Tsuji oxidation-biotransamination sequential process", Advanced Synthesis & Catalysis (2019); 361(11): 2582-2593; 97 pages with Supporting Information.

Goodman et al., "Treatment of generalized anxiety disorder with escitalopram: pooled results from double-blind, placebo-controlled trials", Journal of Affective Disorders (2005); 87(2-3): 161-167. doi: 10.1016/j.jad.2004.11.011.

Goodwin. "An intravenous self-administration procedure for assessing the reinforcing effects of hallucinogens in nonhuman primates", Journal of Pharmacological and Toxicological Methods (2016); 82: 31-36. doi: 10.1016/j.vascn.2016.07.004. Epub Jul. 26, 2016.

Graham et al., "The actions of d-lysergic acid diethylamide (LSD-25)", Part 1, General Pharmacology, Journal of the Faculty of Medicine Baghdad, Iraq (1954); 18: 1-10; 11 pages.

Greden. "The burden of recurrent depression: Causes, consequences, and future prospects", Journal of Clinical Psychiatry (2001); 62(suppl 22): 5-9.

Green et al., "Defining the histamine H2-receptor in brain: the interaction with LSD", NIDA Research Monogram (1978); 22: 38-59.

Greenberg et al., "The economic burden of adults with major depressive disorder in the United States (2005 and 2010)", Journal of Clinical Psychiatry (2015); 76(2): 155-162. doi: 10.4088/JCP.14m09298.

Greiner et al., "Pharmacotherapy of psychiatric inpatients with adjustment disorder: current status and changes between 2000 and 2016", European Archives of Psychiatry and Clinical Neuroscience (2020); 270(1): 107-117. doi: 10.1007/s00406-019-01058-1. Epub Aug. 22, 2019.

Gresch et al., "Behavioral tolerance to lysergic acid diethylamide is associated with reduced serotonin-2A receptor signaling in rat cortex", Neuropsychopharmacology (2005); 30: 1693-1702. doi: 10.1038/sj.npp.1300711.

Griffiths et al., "Mystical-type experiences occasioned by psilocybin mediate the attribution of personal meaning and spiritual significance 14 months later", Journal of Psychopharmacology (2008); 22(6): 621-632. doi: 10.1177/0269881108094300. Epub Jul. 1, 2008.

Griffiths et al., "Psilocybin produces substantial and sustained decreases in depression and anxiety in patients with life-threatening cancer: a randomized double-blind trial", Journal of Psychopharmacology (2016); 30: 1181-1197. doi: 10.1177/0269881116675513.

Grob et al., "Pilot study of psilocybin treatment for anxiety in patients with advanced-stage cancer", Archives of General Psychiatry (2011); 68(1): 71-78. doi: 10.1001/archgenpsychiatry.2010.116. Epub Sep. 6, 2010.

Grof et al., "LSD-assisted psychotherapy in patients with terminal cancer", International Pharmacopsychiatry (1973); 8(3): 129-144. doi: 10.1159/000467984.

Guy. "ECDEU Assessment Manual for Psychopharmacology, Clinical Global Impressions (CGI)", U.S. Department of Health and Human Services, Public Health Service, Alcohol Drug Abuse and Mental Health Administration, NIMH Psychopharmacology Research Branch, Rockville, MD (1976); pp. 218-222; 11 pages.

Haden et al., "LSD Overdoses: Three Case Reports", Journal of Studies on Alcohol and Drugs (Jan. 2020); 81(1): 115-118.

Halberstadt. "Recent advances in the neuropsychopharmacology of serotonergic hallucinogens", Behavioural Brain Research (2015); 277: 99-120. doi: 10.1016/j.bbr.2014.07.016. Epub Jul. 15, 2014.

Haley et al., "Brain concentrations of LSD-25 (delysid) after intracerebral or intravenous administration in conscious animals", Experientia (1957); 13(5): 199-200.

(56) References Cited

OTHER PUBLICATIONS

Hanaway. "Lysergic acid diethylamine: Effects on the developing mouse lens", Science (1969); 164: 574-575. doi: 10.1126/science.164.3879.574.

Handforth. "Harmaline tremor: underlying mechanisms in a potential animal model of essential tremor", Tremor and Other Hyperkinetic Movements (2012); 2: 14 pages. doi: 10.7916/D8TD9W2P. Epub Sep. 12, 2012.

Hartford et al., "Duloxetine as an SNRI treatment for generalized anxiety disorder: results from a placebo and active-controlled trial", International Clinical Psychopharmacology (2007); 22(3): 167-174. doi: 10.1097/YIC.0b013e32807fb1b2.

Hashimoto et al., "Actions of D-lysergic acid diethylamide (LSD) and its derivatives on 5-hydroxytryptamine receptors in the isolated uterine smooth muscle of the rat", European Journal of Pharmacology (1977); 45(4): 341-348. doi: 10.1016/0014-2999(77)90273-4.

Herdman et al., "Development and preliminary testing of the new five-level version of EQ-5D (EQ-5D-5L)", Quality of Life Research (2011); 20(10): 1727-1736. doi: 10.1007/s11136-011-9903-x. Epub Apr. 9, 2011.

Hidalgo et al., "An effect-size analysis of pharmacologic treatments for generalized anxiety disorder", Journal of Psychopharmacology (2007); 21(8): 864-872. doi: 10.1177/0269881107076996.

Hintzen et al., "The pharmacology of LSD: a critical review", Oxford University Press: Oxford (2010); pp. 258-259; 2 pages. Abstract Only.

Hirst et al., "Differences in the central nervous system distribution and pharmacology of the mouse 5-hydroxytryptamine-6 receptor compared with rat and human receptors investigated by radioligand binding, site-directed mutagenesis, and molecular modeling", Molecular Pharmacology (2003); 64(6): 1295-1308. doi: 10.1124/mol.64.6.1295.

Hoehn et al., "Experimental evaluation of the generalized vibrational theory of G protein-coupled receptor activation", Proceedings of the National Academy of Sciences (2017); 114(22): 5595-5600. doi: 10.1073/pnas.1618422114. Epub May 12, 2017.

Hoff et al., "Allgemeine Gesichtspunkte zur Pharmakopsychiatrie", In: Bradley PB, ed. Neuro-Psychopharmacology. Amsterdam: Elsevier (1959); pp. 61-70, 91, and 326-327; 46 pages with English translation.

Hoffer. "D-Lysergic acid diethylamide (LSD): A review of its present status", Clinical Pharmacology & Therapeutics (1965); 6: 183-255. doi: 10.1002/cpt196562183.

Hoffmann et al., "Synthesis and LSD-like discriminative stimulus properties in a series of N (6)-alkyl norlysergic acid N, N-diethylamide derivatives", Journal of Medicinal Chemistry (1985); 28(9): 1252-1255. doi: 10.1021/jm00147a022.

Hoffmann. "Synthesis and pharmacological evaluation of N (6)-alkyl norlysergic acid N, N-diethylamide derivatives", A Thesis submitted to the Faculty of Purdue University, In partial fulfillment of the Requirements for the Degree of Doctor of Philosophy (Aug. 1987); 24 pages.

Hofmann. "How LSD originated", Journal of Psychedelic Drugs (1979); 11(1-2): 53-60. doi: 10.1080/02791072.1979.10472092.

Holze et al., "Acute dose-dependent effects of lysergic acid diethylamide in a double-blind placebo-controlled study in healthy subjects", Neuropsychopharmacology (2021); 46(3): 537-544. doi: 10.1038/s41386-020-00883-6. Epub Oct. 15, 2020.

Holze et al., "Distinct acute effects of LSD, MDMA, and D-amphetamine in healthy subjects", Neuropsychopharmacology (2020); 45(3): 462-471. doi: 10.1038/s41386-019-0569-3. Epub Nov. 16, 2019.

Holze et al., "Lysergic acid diethylamide-assisted therapy in patients with anxiety with and without a life-threatening illness: A randomized, double-blind, placebo-controlled phase II study", Biological Psychiatry (2023); 93(3): 215-223. doi: 10.1016/j.biopsych.2022.08.025. Epub Sep. 5, 2022.

Holze et al., "Pharmacokinetics and Pharmacodynamics of Lysergic Acid Diethylamide Microdoses in Healthy Participants." Clinical Pharmacology & Therapeutics (Mar. 2021); 109(3): 658-666. doi: 10.1002/cpt.2057. Epub Oct. 18, 2020.

Holze et al., "Pharmacokinetics and subjective effects of a novel oral LSD formulation in healthy subjects", British Journal of Clinical Pharmacology (2019); 85(7): 1474-1483. doi: 10.1111/bcp.13918. Epub Apr. 29, 2019.

Huang et al., "Drug discrimination and receptor binding studies of N-isopropyl lysergamide derivatives", Pharmacology Biochemistry and Behavior (1994); 47(3): 667-673. doi: 10.1016/0091-3057(94)90172-4.

Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time", The Journal of Neuroscience (May 11, 2011); 31(19): 7190-7198. doi: 10.1523/JNEUROSCI.1171-11.2011.

Hutten et al., "Low doses of LSD acutely increase BDNF blood plasma levels in healthy volunteers", ACS Pharmacology & Transitional Science Journal (2021); 4(2): 461-466. doi: 10.1021/acsptsci.0c00099.

Hutten et al., "Mood and cognition after administration of low LSD doses in healthy volunteers: A placebo controlled dose-effect finding study", European Neuropsychopharmacology (Oct. 2020); 41: 81-91. doi: 10.1016/j.euroneuro.2020.10.002. Epub Oct. 17, 2020.

Idanpaan-Heikkila et al., "14C-lysergide in early pregnancy", The Lancet (Jul. 26, 1969); 294(7613): 221; 1 page. doi: 10.1016/s0140-6736(69)91466-4.

Idanpaan-Heikkila et al., "Total body kinetics and placental transfer of labeled LSD in mice", Drug Dependence, Austin & London (1970); pp. 55-66; 13 pages.

Inoue et al., "Effects of inducers and/or inhibitors on metabolism of lysergic acid diethylamide in rat liver microsomes", Xenobiotica (Dec. 1980); 10(12): 913-920. doi: 10.3109/00498258009033825.

Inoue et al., "Enzymic formation of dehydrogenated and hydroxylated metabolites from lysergic acid diethylamide by rat liver microsomes", Xenobiotica (May 1980); 10(5): 343-348. doi: 10.3109/00498258009033766.

International Preliminary Report on Patentability for International Application No. PCT/US2022/027181, by Mind Medicine, Inc., mailed Nov. 16, 2023, 6 pages.

International Search Report and Written Opinion for International Application No. PCT/US2022/027181, by Mind Medicine, Inc., mailed Jul. 29, 2022, 11 pages.

International Search Report and Written Opinion for International Application No. PCT/US2024/022901, by Mind Medicine, Inc., mailed Aug. 5, 2024, 6 pages.

Iravani et al. ,"3, 4-methylenedioxymethamphetamine (ecstasy) inhibits dyskinesia expression and normalizes motor activity in 1-methyl-4-phenyl-1, 2, 3, 6-tetrahydropyridine-treated primates", Journal of Neuroscience (2003); 23(27): 9107-9115. doi: 10.1523/JNEUROSCI.23-27-09107.2003.

Irwin et al., "Chromosomal abnormalities in leukocytes from LSD-25 users", Science (1967); 157(3786): 313-314.

Isbell. "Comparison of the reactions induced by psilocybin and LSD-25 in man", Psychopharmacologia (1959); 1: 29-38. doi: 10.1007/BF00408109.

Ishii et al., "Studies of lysergic acid diethylamide and related compounds. Part 8. Structural identification of new metabolites of lysergic acid diethylamide obtained by microbial transformation using Streptomyces roseochromogenes", Journal of the Chemical Society, Perkin Transactions 1 (1980); 4: 902-905.

Ishii et al., "Studies on lysergic acid diethylamide and related compounds. VII. Microbial transformation of lysergic acid diethylamide and related compounds", Chemical and Pharmaceutical Bulletin (1979); 27(7): 1570-1575. doi: 10.1248/cpb.27.1570.

Issakidis et al., "Pretreatment attrition and dropout in an outpatient clinic for anxiety disorders", Acta Psychiatrica Scandinavica (2004); 109(6): 426-433. doi: 10.1111/j.1600-0047.2004.00264.x.

Jagiello et al., "Mouse germ cells and LSD-25", Cytogenics (1969); 8: 136-147. doi: 10.1159/000130030.

Jankovic. "Parkinson's disease: clinical features and diagnosis", Journal of Neurology, Neurosurgery & Psychiatry (2008); 79(4): 368-376. doi: 10.1136/jnnp.2007.131045.

(56) References Cited

OTHER PUBLICATIONS

Johansen et al., "Psychedelics not linked to mental health problems or suicidal behavior: a population study", Journal of Psychopharmacology (2015); 29(3): 270-279. doi: 10.1177/0269881114568039. Epub Mar. 5, 2015.

Johnson et al., "Emetic activity of reduced lysergamides", Journal of Medicinal Chemistry (1973); 16(5): 532-537. doi: 10.1021/jm00263a028.

Johnson et al., "Long-term follow-up of psilocybin-facilitated smoking cessation", The American Journal of Drug and Alcohol Abuse (2017); 43(1): 55-60. doi: 10.3109/00952990.2016.1170135. Epub Jul. 21, 2016. Erratum in: Am J Drug Alcohol Abuse. Jan. 2017;43(1):127. doi: 10.1080/00952990.2016.1277105.

Johnson et al., "Pilot study of the 5-HT2AR agonist psilocybin in the treatment of tobacco addiction", Journal of Psychopharmacology (2014); 28(11): 983-992. doi: 10.1177/0269881114548296. Epub Sep. 11, 2014.

Johnston et al., "Monitoring the future, national survey results on drug use, 1975-2015: vol. 2. College students and adults ages 19-55", Ann Arbor: Institute for Social Research, The University of Michigan (2016) [online] http://monitoringthefuture.org/pubs.html#monographs (Access Date: Nov. 1, 2021); 453 pages.

Judd et al., "A prospective 12-year study of subsyndromal and syndromal depressive symptoms in unipolar major depressive disorders", Archives of General Psychiatry (Aug. 1998); 55: 694-700. doi: 10.1001/archpsyc.55.8.694.

Kaelen et al., "LSD enhances emotional response to music", Psychopharmacology (Aug. 2015); 232(19): 3607-3614. doi: 10.1007/s00213-015-4014-y. Epub Aug. 11, 2015.

Kaelen et al., "LSD modulates music-induced imagery via changes in parahippocampal connectivity", European Neuropsychopharmacology (2016); 26: 1099-1109. doi: 10.1016/j.euroneuro.2016.03.018. Epub Apr. 12, 2016.

Kargbo. "Current Trends in Psychedelic Science: Integrating Modified Lysergic Acid Derivatives and Psilocybin in Modern Medicine", ACS Medicinal Chemistry Letters (2024); 15(9): 1443-1445. doi: 10.1021/acsmedchemlett.4c00414.

Kariuki-Nyuthe et al., "Anxiety and Related Disorders and Physical Illness", In: Sartorius N, Holt RIG, Maj M (eds): Comorbidity of Mental and Physical Disorders, Key Issues Ment Health, Basel, Karger (2015); 179: 81-87.

Kato et al., "LSD-25 and genetic damage", Diseases of the Nervous System (1969); 30: 42-46.

Kavan et al., "Generalized anxiety disorder: Practical assessment and management", American Family Physician (May 1, 2009); 79(9): 785-791.

Kessler et al., "Lifetime prevalence and age-of-onset distributions of DSM-IV disorders in the National Comorbidity Survey Replication", Archives of General Psychiatry (Jun. 2005); 62(6): 593-602. doi: 10.1001/archpsyc.62.6.593.

Kessler et al., "Prevalence, severity, and comorbidity of 12-month DSM-IV disorders in the National Comorbidity Survey Replication", Archives of General Psychiatry (2005); 62: 617-627. doi: 10.1001/archpsyc.62.6.617.

Kessler et al., "The epidemiology of generalized anxiety disorder", Psychiatric Clinics of North America (2001); 24(1): 19-39. doi: 10.1016/s0193-953x(05)70204-5.

Klette et al., "Metabolism of Lysergic Acid Diethylamide (LSD) to 2-Oxo-3-Hydroxy LSD (O-H-LSD) in Human Liver Microsomes and Cryopreserved Human Hepatocytes", Journal of Analytical Toxicology (2000); 24(7): 550-556. doi: 10.1093/jat/24.7.550.

Klock et al., "Coma, hyperthermia and bleeding associated with massive LSD overdose. A report of eight cases", The Western Journal of Medicine (1974); 120(3): 183-188.

Koelle. "The pharmacology of mescaline and D-lysergic acid diethylamide (LSD)", New England Journal of Medicine (1958); 258(1): 25-32. doi: 10.1056/NEJM195801022580106.

Kraehenmann et al., "Dreamlike effects of LSD on waking imagery in humans depend on serotonin 2A receptor activation", Psychopharmacology (Berl) (2017); 234: 2031-2046. doi: 10.1007/s00213-017-4610-0. Epub Apr. 7, 2017.

Kraehenmann et al., "LSD Increases Primary Process Thinking via Serotonin 2A Receptor Activation", Frontiers in Pharmacology (2017); 8: 814; 9 pages. doi: 10.3389/fphar.2017.00814.

Krall et al., "Marked decrease of LSD-induced stimulus control in serotonin transporter knockout mice", Pharmacology Biochemistry and Behavior (2008); 88: 349-357. doi: 10.1016/j.pbb.2007.09.006. Epub Sep. 14, 2007.

Krebs et al., "Lysergic acid diethylamide (LSD) for alcoholism: meta-analysis of randomized controlled trials", Journal of Psychopharmacology (2012); 26(7): 994-1002. doi: 10.1177/0269881112439253. Epub Mar. 8, 2012.

Krebs et al., "Over 30 million psychedelic users in the United States", F1000 Research (2013); 2: 98; 5 pages. doi: 10.12688/f1000research.2-98.v1.

Krebs et al., "Psychedelics and mental health: a population study", PLoS One (2013); 8(8): e63972; 9 pages. doi: 10.1371/journal.pone.0063972.

Krebs-Thomson et al., "Effects of hallucinogens on locomotor investigatory activity and patterns: Influence of 5-HT2A and 5-HT2C receptors," Neuropsychopharmacology (1998); 18(5): 339-351. doi: 10.1016/S0893-133X(97)00164-4.

Kristensen. "LSD treatment combined with parenteral Ritalin therapy." Nord Psykiatr Tidsskr (1962); 16: 111-116; 14 pages with English machine translation.

Krus et al., "Inhibitory effects of steroids on LSD-25 action in man", Life Science (1967); 6: 691-701. doi: 10.1016/0024-3205(67)90124-5.

Krus et al., "The influence of progesterone on behavioral changes induced by lysergic acid diethylamide (LSD-25) in normal males", Psychopharmacologia (1961); 2: 177-184. doi: 10.1007/BF00407977.

Kulkarni et al., "Modification by levo-propranolol of tremors induced by harmine in mice", Experientia (1979); 35(12): 1627-1628. doi: 10.1007/BF01953232.

Kupferschmidt. "High hopes", Science (Jul. 4, 2014); 345(6192): 18-23. doi: 10.1126/science.345.6192.18.

Kyzar et al., "Effects of LSD on grooming behavior in serotonin transporter heterozygous (Sert+/-) mice", Behavioural Brain Research (2016); 296: 47-52. doi: 10.1016/j.bbr.2015.08.018. Epub Sep. 2015.

Lambe et al., "Hallucinogen-induced UP states in the brain slice of rat prefrontal cortex: role of glutamate spillover and NR2B-NMDA receptors", Neuropsychopharmacology (2006); 31: 1682-1689. doi: 10.1038/sj.npp.1300944. Epub Nov. 2, 2005.

Lanz et al., "Distribution of lysergic acid diethylamide in the organism", Helvetica Physiologica et Pharmacologica Acta (1955); 13(3): 207-216; 10 pages with English summary.

Lebedev et al., "LSD-induced entropic brain activity predicts subsequent personality change", Human Brain Mapping (2016); 37: 3203-3213. doi: 10.1002/hbm.23234. Epub May 6, 2016.

Lenze et al., "Efficacy and tolerability of citalopram in the treatment of late-life anxiety disorders: Results from an 8-week randomized, placebo-controlled trial", American Journal of Psychiatry (Jan. 2005); 162(1): 146-150. doi: 10.1176/appi.ajp.162.1.146.

Leonard et al., "Does getting high hurt? Characterization of cases of LSD and psilocybin-containing mushroom exposures to national poison centers between 2000 and 2016", Journal of Psychopharmacology (Dec. 2018); 32(12): 1286-1294. doi: 10.1177/0269881118793086. Epub Sep. 5, 2018.

Levy. "Diazepam for L.S.D. intoxication", Lancet (1971); 1: 1297; 1 page. doi: 10.1016/s0140-6736(71)91810-1.

Lewis. "A Medicinal Chemistry Investigation of 3,4-Methylenedioxymethamphetamine(MDMA)", Chemistry, School of Biomedical, Biomedical and Chemical Sciences, Thesis presented for the degree of Doctor of Philosophy of The University of Western Australia (2011), 216 pages.

(56) References Cited

OTHER PUBLICATIONS

Liechti et al., "Alterations of consciousness and mystical-type experiences after acute LSD in humans", Psychopharmacology (2017); 234: 1499-1510. doi: 10.1007/s00213-016-4453-0. Epub Oct. 7, 2016.

Liechti. "Modern clinical research on LSD", Neuropsychopharmacology (2017); 42(11): 2114-2127. doi: 10.1038/npp.2017.86. Epub Apr. 27, 2017.

Llabres et al., "Molecular basis of the selective binding of MDMA enantiomers to the alpha4beta2 nicotinic receptor subtype: synthesis, pharmacological evaluation and mechanistic studies", European Journal of Medicinal Chemistry (2014); 81: 35-46; 28 pages with Supporting Information.

Llorca et al., "Efficacy and safety of hydroxyzine in the treatment of generalized anxiety disorder: A 3-month double-blind study", Journal of Clinical Psychiatry (2002); 63(11): 1020-1027. doi: 10.4088/jcp.v63n1112.

Long. "Does LSD induce chromosomal damage and malformations? A review of the literature", Teratology (1972); 6(1): 75-90. doi: 10.1002/tera.1420060110.

Long et al., "Rhythmicity without synchrony in the electrically uncoupled inferior olive", Journal of Neuroscience (2002); 22(24): 10898-10905. doi: 10.1523/JNEUROSCI.22-24-10898.2002.

Luethi et al., "Cytochrome P450 enzymes contribute to the metabolism of LSD to nor-LSD and 2-oxo-3-hydroxy-LSD: Implications for clinical LSD use", Biochemical Pharmacology (2019); 164: 129-138. doi: 10.1016/j.bcp.2019.04.013. Epub Apr. 11, 2019.

Ly et al., "Psychedelics promote structural and functional neural plasticity", Cell Reports (2018); 23(11): 3170-3182. doi: 10.1016/j.celrep.2018.05.022.

Lykos Therapeutics, "Lykos Therapeutics Shares Updates on USPTO Patent Filings", News Release Archive (Jan. 17, 2025) [online] https://news.lykospbc.com/2025-01-17-Lykos-Therapeutics-Shares-Updates-on-USPTO-Patent-Filings?printable (Access Date: Jan. 23, 2025); 2 pages.

Maastricht University, "LSD microdosing", NTR-new: NL6907, NTR-old: NTR7102 (Jan. 5, 2018), 5 pages.

Mackenzie et al., "Chromosomal abnormalities in human leukocytes exposed to LSD in culture", Mammalian Chromosome Newsletter (1968); 9: 212-217.

Magano. "Large-scale amidations in process chemistry: practical considerations for reagent selection and reaction execution", Organic Process Research & Development (2022); 26(6): 1562-1689.

Maier et al., "The Hamilton Anxiety Scale: Reliability, validity and sensitivity to change in anxiety and depressive disorders", Journal of Affective Disorders (1988); 14: 61-68. doi: 10.1016/0165-0327(88)90072-9.

Malhi et al., "Depression", Lancet. Seminar (Nov. 24, 2018); 392(10161): 2299-2312. doi: 10.1016/S0140-6736(18)31948-2. Epub Nov. 2, 2018.

Marek et al., "LSD and the phenethylamine hallucinogen DOI are potent partial agonists at 5-HT2A receptors on interneurons in rat piriform cortex", Journal of Pharmacology and Experimental Therapeutics (1996); 278: 1373-1382.

Marona-Lewicka et al., "An animal model of schizophrenia based on chronic LSD administration: Old idea, new results", Neuropharmacology (2011); 61: 503-512. doi: 10.1016/j.neuropharm.2011.02.006. Epub Feb. 23, 2011.

Marona-Lewicka et al., "Complex stimulus properties of LSD: a drug discrimination study with α2-adrenoceptor agonists and antagonists", Psychopharmacology (1995); 120(4): 384-391. doi: 10.1007/BF02245809.

Marona-Lewicka et al., "Distinct temporal phases in the behavioral pharmacology of LSD: dopamine D 2 receptor-mediated effects in the rat and implications for psychosis", Psychopharmacology (2005); 180: 427-435. doi: 10.1007/s00213-005-2183-9. Epub Feb. 19, 2005.

Marona-Lewicka et al., "Dopamine D4 receptor involvement in the discriminative stimulus effects in rats of LSD, but not the phenethylamine hallucinogen DOI", Psychopharmacology (2009); 203: 265-277. doi: 10.1007/s00213-008-1238-0. Epub Jul. 6, 2008.

Marona-Lewicka et al., "Further evidence that the delayed temporal dopaminergic effects of LSD are mediated by a mechanism different than the first temporal phase of action." Pharmacology, Biochemistry and Behavior (2007); 87(4): 453-461. doi: 10.1016/j.pbb.2007.06.001. Epub Jun. 14, 2007.

Martin et al., "Chronic LSD alters gene expression profiles in the mPFC relevant to schizophrenia", Neuropharmacology (2014); 83: 1-8. doi: 10.1016/j.neuropharm.2014.03.013. Epub Apr. 3, 2014.

Martin et al., "Harmaline-induced tremor as a potential preclinical screening method for essential tremor medications", Movement Disorders (2005); 20(3): 298-305. doi: 10.1002/mds.20331.

Martin et al., "The effects of hallucinogens on gene expression", Current Topics in Behavioral Neurosciences (2017); 36: 137-158. doi: 10.1007/7854_2017_479.

Mcgahuey et al., "The Arizona Sexual Experience Scale (ASEX): reliability and validity", Journal of Sex and Marital Therapy (2000); 26(1): 25-40. doi: 10.1080/009262300278623.

Meehan et al., "LSD produces conditioned place preference in male but not female Fawn Hooded rats", Pharmacology Biochemistry and Behavior (1998); 59(1): 105-108. doi: 10.1016/s0091-3057(97)00391-2.

Meert et al., "Risperidone (R 64 766), a potent and complete LSD antagonist in drug discrimination by rats", Psychopharmacology (1989); 97(2): 206-212. doi: 10.1007/BF00442251.

Milburn et al., "Characterization of [3H]Quipazine Binding to 5 Hydroxytryptamine3 Receptors in Rat Brain Membranes", Journal of Neurochemistry (1989); 52(6): 1787-1792.

Miller et al., "Primate trace amine receptor 1 modulation by the dopamine transporter", Journal of Pharmacology and Experimental Therapeutics (2005); 313(3): 983-994. doi: 10.1124/jpet.105.084459. Epub Mar. 11, 2005.

Mind Medicine, Inc., "A Dose-Finding Study of MM-120 (LSD D-Tartrate) for the Treatment of Anxiety Symptoms" ClinicalTrials.gov ID NCT05407064, version 1, Jun. 1, 2022, 12 pages.

Mind Medicine, Inc., "A Dose-Finding Study of MM-120 (LSD D-Tartrate) for the Treatment of Anxiety Symptoms" ClinicalTrials.gov Id NCT05407064, version 10, Nov. 15, 2022, 15 pages.

Mind Medicine, Inc., "A Dose-Finding Study of MM-120 (LSD D-Tartrate) for the Treatment of Anxiety Symptoms" ClinicalTrials.gov Id NCT05407064, version 11, Nov. 15, 2022, 15 pages.

Mind Medicine, Inc., "A Dose-Finding Study of MM-120 (LSD D-Tartrate) for the Treatment of Anxiety Symptoms" ClinicalTrials.gov ID NCT05407064, version 12, Nov. 17, 2022, 15 pages.

Mind Medicine, Inc., "A Dose-Finding Study of MM-120 (LSD D-Tartrate) for the Treatment of Anxiety Symptoms" ClinicalTrials.gov Id NCT05407064, version 13, Dec. 12, 2022, 16 pages.

Mind Medicine, Inc., "A Dose-Finding Study of MM-120 (LSD D-Tartrate) for the Treatment of Anxiety Symptoms" ClinicalTrials.gov ID NCT05407064, version 14, Jan. 20, 2023, 16 pages.

Mind Medicine, Inc., "A Dose-Finding Study of MM-120 (LSD D-Tartrate) for the Treatment of Anxiety Symptoms" ClinicalTrials.gov ID NCT05407064, version 15, Jan. 27, 2023, 16 pages.

Mind Medicine, Inc., "A Dose-Finding Study of MM-120 (LSD D-Tartrate) for the Treatment of Anxiety Symptoms" ClinicalTrials.gov ID NCT05407064, version 16, Feb. 3, 2023, 16 pages.

Mind Medicine, Inc., "A Dose-Finding Study of MM-120 (LSD D-Tartrate) for the Treatment of Anxiety Symptoms" ClinicalTrials.gov ID NCT05407064, version 17, Feb. 10, 2023, 16 pages.

Mind Medicine, Inc., "A Dose-Finding Study of MM-120 (LSD D-Tartrate) for the Treatment of Anxiety Symptoms" ClinicalTrials.gov ID NCT05407064, version 18, Mar. 15, 2023, 17 pages.

Mind Medicine, Inc., "A Dose-Finding Study of MM-120 (LSD D-Tartrate) for the Treatment of Anxiety Symptoms" ClinicalTrials.gov ID NCT05407064, version 19, Jun. 28, 2023, 17 pages.

Mind Medicine, Inc., "A Dose-Finding Study of MM-120 (LSD D-Tartrate) for the Treatment of Anxiety Symptoms" ClinicalTrials.gov ID NCT05407064, version 2, Jun. 15, 2022, 12 pages.

Mind Medicine, Inc., "A Dose-Finding Study of MM-120 (LSD D-Tartrate) for the Treatment of Anxiety Symptoms" ClinicalTrials.gov ID NCT05407064, version 20, Jul. 28, 2023, 17 pages.

(56)         References Cited

OTHER PUBLICATIONS

Mind Medicine, Inc., "A Dose-Finding Study of MM-120 (LSD D-Tartrate) for the Treatment of Anxiety Symptoms" ClinicalTrials. gov ID NCT05407064, version 21, Aug. 1, 2023, 17 pages.
Mind Medicine, Inc., "A Dose-Finding Study of MM-120 (LSD D-Tartrate) for the Treatment of Anxiety Symptoms" ClinicalTrials. gov ID NCT05407064, version 22, Sep. 13, 2023, 13 pages.
Mind Medicine, Inc., "A Dose-Finding Study of MM-120 (LSD D-Tartrate) for the Treatment of Anxiety Symptoms" ClinicalTrials. gov ID NCT05407064, version 23, Oct. 25, 2023, 13 pages.
Mind Medicine, Inc., "A Dose-Finding Study of MM-120 (LSD D-Tartrate) for the Treatment of Anxiety Symptoms" ClinicalTrials. gov ID NCT05407064, version 24, Dec. 19, 2023, 13 pages.
Mind Medicine, Inc., "A Dose-Finding Study of MM-120 (LSD D-Tartrate) for the Treatment of Anxiety Symptoms" ClinicalTrials. gov ID NCT05407064, version 3, Aug. 4, 2022, 12 pages.
Mind Medicine, Inc., "A Dose-Finding Study of MM-120 (LSD D-Tartrate) for the Treatment of Anxiety Symptoms" ClinicalTrials. gov ID NCT05407064, version 4, Sep. 11, 2022, 13 pages.
Mind Medicine, Inc., "A Dose-Finding Study of MM-120 (LSD D-Tartrate) for the Treatment of Anxiety Symptoms" ClinicalTrials. gov ID NCT05407064, version 5, Sep. 15, 2022, 13 pages.
Mind Medicine, Inc., "A Dose-Finding Study of MM-120 (LSD D-Tartrate) for the Treatment of Anxiety Symptoms" ClinicalTrials. gov ID NCT05407064, version 6, Sep. 28, 2022, 14 pages.
Mind Medicine, Inc., "A Dose-Finding Study of MM-120 (LSD D-Tartrate) for the Treatment of Anxiety Symptoms" ClinicalTrials. gov ID NCT05407064, version 7, Oct. 21, 2022, 14 pages.
Mind Medicine, Inc., "A Dose-Finding Study of MM-120 (LSD D-Tartrate) for the Treatment of Anxiety Symptoms" ClinicalTrials. gov ID NCT05407064, version 8, Nov. 11, 2022, 15 pages.
Mind Medicine, Inc., "A Dose-Finding Study of MM-120 (LSD D-Tartrate) for the Treatment of Anxiety Symptoms" ClinicalTrials. gov ID NCT05407064, version 9, Nov. 9, 2022, 15 pages.
Mind Medicine, Inc., "A Study to Assess 18-Methoxycoronaridine (18-MC HCI) in Healthy Volunteers" ClinicalTrials.gov ID NCT04292197, version 10, Jan. 4, 2022, 11 pages.
Mind Medicine, Inc., "A Study to Assess 18-Methoxycoronaridine (18-MC HCI) in Healthy Volunteers" ClinicalTrials.gov ID NCT04292197, version 7, Mar. 11, 2021, 12 pages.
Mind Medicine, Inc., "A Study to Assess 18-Methoxycoronaridine (18-MC HCI) in Healthy Volunteers" ClinicalTrials.gov ID NCT04292197, version 9, Aug. 3, 2021, 12 pages.
Mind Medicine, Inc., "Safety and Efficacy of Low Dose MM-120 for ADHD Proof of Concept Trial" ClinicalTrials.gov ID NCT05200936, version 1, Jan. 7, 2022, 11 pages.
Mind Medicine, Inc., "Safety and Efficacy of Low Dose MM-120 for ADHD Proof of Concept Trial" ClinicalTrials.gov ID NCT05200936, version 2, Jun. 15, 2022, 11 pages.
Mind Medicine, Inc., "Safety and Efficacy of Low Dose MM-120 for ADHD Proof of Concept Trial" ClinicalTrials.gov ID NCT05200936, version 3, Jul. 31, 2023, 11 pages.
Mind Medicine, Inc., "Safety and Efficacy of Low Dose MM-120 for ADHD Proof of Concept Trial" ClinicalTrials.gov ID NCT05200936, version 4, Oct. 24, 2023, 10 pages.
Mind Medicine, Inc., "Safety and Efficacy of Low Dose MM-120 for ADHD Proof of Concept Trial" ClinicalTrials.gov ID NCT05200936, version 5, Jan. 12, 2024, 10 pages.
Mind Medicine, Inc., "Phase I trial: MM-120-101", ISRCTN The UK's Clinical Study Registry, ISRCTN11052603 (May 14, 2024), 5 pages. doi.org/10.1186/ISRCTN11052603.
Mind Medicine, Inc., "Phase I trial: MM-120-102", ISRCTN The UK's Clinical Study Registry, ISRCTN15997848 (May 17, 2024); 5 pages. doi.org/10.1186/ISRCTN15997848.
Minuzzi et al., "Interaction between LSD and dopamine D2/3 binding sites in pig brain", Synapse (2005); 56: 198-204. oi: 10.1002/syn.20141.
Mittman et al., "Dissociation of multiple effects of acute LSD on exploratory behavior in rats by ritanserin and propranolol", Psychopharmacology (1991); 105: 69-76. doi: 10.1007/BF02316866.

Monte et al., "Stereoselective LSD-like activity in a series of d-lysergic acid amides of (R)-and (S)-2-aminoalkanes", Journal of Medicinal Chemistry (1995); 38(6): 958-966. doi: 10.1021/jm00006a015.
Montgomery et al., "A new depression scale designed to be sensitive to change", The British Journal of Psychiatry (1979); 134: 382-389. doi: 10.1192/bjp.134.4.382.
Moreno et al., "Chronic treatment with LY341495 decreases 5-HT2A receptor binding and hallucinogenic effects of LSD in mice", Neuroscience Letters (2013); 536: 69-73. doi: 10.1016/j.neulet.2012. 12.053. Epub Jan. 16, 2013.
Mueller et al., "Acute effects of LSD on amygdala activity during processing of fearful stimuli in healthy subjects", Translational Psychiatry (2017); 7: e1084; 5 pages. doi: 10.1038/tp.2017.54.
Mueller et al., "Altered network hub connectivity after acute LSD administration", NeuroImage: Clinical (2018); 18: 694-701. doi: 10.1016/j.nicl.2018.03.005. eCollection 2018.
Multidisciplinary Association for Psychedelic Studies "Lysergic Acid Diethylamide (LSD)-Assisted Psychotherapy in People With Illness-related Anxiety" ClinicalTrials.gov ID NCT00920387, version 12, Feb. 16, 2022, 25 pages.
Multidisciplinary Association for Psychedelic Studies "Lysergic Acid Diethylamide (LSD)-Assisted Psychotherapy in People With Illness-related Anxiety" ClinicalTrials.gov ID NCT00920387, version 13, Jun. 14, 2022, 27 pages.
Multidisciplinary Association for Psychedelic Studies "Lysergic Acid Diethylamide (LSD)-Assisted Psychotherapy in People With Illness-related Anxiety" ClinicalTrials.gov ID NCT00920387, version 9, Apr. 16, 2014, 14 pages.
Muneer. "Effects of LSD on human chromosomes", Mutation Research (1978); 51(3): 403-410. doi: 10.1016/0027-5107(78)90128-8.
Murakami et al., "Behavioral thermoregulation in rats during hyperthermia induced by lysergic acid diethylamide", Neuroscience Letters (1980); 20(1): 105-108. doi: 10.1016/0304-3940(80)90242-6.
Nakahara et al., "Studies on lysergic acid diethylamide and related compounds. 3. Improvement of amidation of lysergic acid (author's transl)", Yakugaku zasshi: Journal of the Pharmaceutical Society of Japan (1974); 94(3): 407-412. doi: 10.1248/yakushi1947.94.3_407.
Nakahara et al., "Studies on Lysergic Acid Diethylamide and Related Compounds. I. Synthesis of d-N6-Demethyl-lysergic Acid Diethylamide", Chemical and Pharmaceutical Bulletin (1971); 19(11): 2337-2341.
National Institute of Mental Health. "What is Depression" OMB Approval #0925-0648 Expiration Date Jun. 30, 2024 [online] https://www.nimh.nih.gov/health/topics/depression (Access Date: May 2024); 3 pages.
National Toxicology Program. "NTP Technical Report on Toxicology and Carcinogenesis Studies of Diethylamine (CAS No. 109-89-7) in F344/N Rats and B6C3F1 Mice (inhalation studies)", NTP TR 566 (Oct. 2011); 179 pages.
Nenajdenko et al., "A new convenient approach to chiral β-aryl (heteroaryl) alkylamines", Tetrahedron: Asymmetry (2001); 12(18): 2517-2527.
Nichols. "Dark classics in chemical neuroscience: lysergic acid diethylamide (LSD)", ACS Chemical Neuroscience (2018); 9(10): 2331-2343. doi: 10.1021/acschemneuro.8b00043. Epub Mar. 1, 2018.
Nichols et al., "Derivatives of 1-(1, 3-benzodioxol-5-yl)-2-butanamine: representatives of a novel therapeutic class", Journal of Medicinal Chemistry (1986); 29(10): 2009-2015. doi: 10.1021/jm00160a035.
Nichols et al., "Dynamic changes in prefrontal cortex gene expression following lysergic acid diethylamide administration", Molecular Brain Research (2003); 111: 182-188. doi: 10.1016/s0169-328x(03)00029-9.
Nichols et al., "Is LSD toxic?", Forensic Science International (2018); 284: 141-145. doi: 10.1016/j.forsciint.2018.01.006. Epub Feb. 2, 2018.
Nichols et al., "Lysergamides of isomeric 2,4-dimethylazetidines map the binding orientation of the diethylamide moiety in the potent

(56) References Cited

OTHER PUBLICATIONS hallucinogenic agent N,N-diethyllysergamide (LSD)", Journal of Medicinal Chemistry (2002); 45: 4344-4349. doi: 10.1021/jm020153s.

Nichols et al., "Molecular genetic responses to lysergic acid diethylamide include transcriptional activation of MAP kinase phosphatase-1, C/EBP-β and ILAD-1, a novel gene with homology to arrestins", Journal of Neurochemistry (2004); 90(3): 576-584. doi: 10.1111/j.1471-4159.2004.02515.x.

Nichols et al., "Stereoselective pharmacological effects of lysergic acid amides possessing chirality in the amide substituent", Behavioural Brain Research (1996); 73(1-2): 117-119. doi: 10.1016/0166-4328(96)00080-0.

Nichols. "Hallucinogens", Pharmacology & Therapeutics (2004); 101(2): 131-181. doi: 10.1016/j.pharmthera.2003.11.002.

Nichols. "Psychedelics", Pharmacological Reviews (2016); 68(2): 264-355. doi: 10.1124/pr.115.011478. Erratum in: Pharmacol Rev. Apr. 2016;68(2):356. doi: 10.1124/pr.114.011478err.

Niwaguchi. "Application of GC/MS to studies on the metabolism of dependence causing drugs. Lysergic acid diethylamide (LSD) and amphetamines", Iyo Masu Kenkyukai Koenshu (1979); 4: 75-82 with English abstract.

Niwaguchi et al., "Studies on enzymatic dealkylation of D-lysergic acid diethylamide (LSD)", Biochemical Pharmacology (1974); 23: 1073-1078. doi: 10.1016/0006-2952(74)90007-0.

Niwaguchi et al., "Studies on the in vitro metabolism of compounds related to lysergic acid diethylamide (LSD)", Biochemical Pharmacology (1974); 23: 3063-3066. doi: 10.1016/0006-2952(74)90282-2.

Norman et al., "[3H] WB4101 labels the 5-HT1A serotonin receptor subtype in rat brain. Guanine nucleotide and divalent cation sensitivity", Molecular Pharmacology (1985); 28: 487-494.

Oberlender et al., "Stereoselective LSD-like activity in d-lysergic acid amides of R- and S-2-aminobutane", Journal of Medicinal Chemistry (1992); 35(2): 203-211. doi: 10.1021/jm00080a001.

Olbrich et al., "LSD and ketanserin and their impact on the human autonomic nervous system", Psychophysiology (2021); 58(6): e13822; 11 pages. doi: 10.1111/psyp.13822. Epub Mar. 27, 2021.

Onuska et al., "Anti-Markovnikov hydroazidation of activated olefins via organic photoredox catalysis", Synlett (2020); 31(1): 55-59; 47 pages with Supplementary Information. doi: 10.1055/s-0039-1690691. Epub Sep. 24, 2019.

Pahnke et al., "LSD-assisted psychotherapy with terminal cancer patients", Current Psychiatry Research (1969); 9: 144-152.

Pahnke et al., "Psychedelic therapy (utilizing LSD) with cancer patients", Journal of Psychedelic Drugs (1970); 3(1): 63-75.

Pan et al., "Animal models of tremor: relevance to human tremor disorders", Tremor and Other Hyperkinetic Movements (2018); 8: 587; 13 pages. doi: 10.7916/D89S37MV.

Papac et al., "Measurement of lysergic acid diethylamide (LSD) in human plasma by gas chromatography/negative ion chemical ionization mass spectrometry", Journal of Analytical Toxicology (1990); 14: 189-190. doi: 10.1093/jat/14.3.189.

Parker. "LSD produces place preference and flavor avoidance but does not produce flavor aversion in rats", Behavioral Neuroscience (1996); 110(3): 503-508. doi: 10.1037//0735-7044.110.3.503.

Passie et al., "The pharmacology of lysergic acid diethylamide: a review", CNS Neuroscience & Therapeutics (2008); 14(4): 295-314. doi: 10.1111/j.1755-5949.2008.00059.x.

Paul. "Involvement of β2-adrenoceptor blockade and 5-hydroxytryptamine mechanism in inhibition of harmaline-induced tremors in rats", European Journal of Pharmacology (1986); 122(1): 111-115. doi: 10.1016/0014-2999(86)90165-2.

Peroutka et al., "The clinical utility of pharmacological agents that act at serotonin receptors", Journal of Neuropsychiatry and Clinical Neurosciences (1989); 1: 253-262. doi: 10.1176/jnp.1.3.253.

Pfaff et al., "Lysergamides revisited", NIDA Research Monograph (1994); 146: 52-73.

Pierce et al., "Hallucinogenic drug interactions with neurotransmitter receptor binding sites in human cortex", Psychopharmacology (1989); 97(1): 118-122. doi: 10.1007/BF00443425.

Pinheiro et al., "Model-based dose finding under model uncertainty using general parametric models", Statistics in Medicine (2014); 33(10): 1646-1661. doi: 10.1002/sim.6052. Epub Dec. 3, 2013.

Páleník et al., "Sex differences in the effects of N,N-diethyllysergamide (LSD) on behavioral activity and prepulse inhibition", Progress in Neuro-Psychopharmacology & Biological Psychiatry (2010); 34: 588-596. doi: 10.1016/j.pnpbp.2010.02.008. Epub Feb. 13, 2010.

Poch et al., "Detection of metabolites of lysergic acid diethylamide (LSD) in human urine specimens: 2-oxo-3-hydroxy-LSD, a prevalent metabolite of LSD", Journal of Chromatography. B Biomed Sci Appl (1999); 724(1): 23-33. doi: 10.1016/s0378-4347(98)00574-x.

Pokorny et al., "LSD acutely impairs working memory, executive functions, and cognitive flexibility, but not risk-based decision-making", Psychological Medicine (2020); 50: 2255-2264. doi: 10.1017/S0033291719002393. Epub Sep. 10, 2019.

Posner et al., "The Columbia-Suicide Severity Rating Scale: initial validity and internal consistency findings from three multisite studies with adolescents and adults." American Journal of Psychiatry (Dec. 2011); 168(12): 1266-1277. doi: 10.1176/appi.ajp.2011.10111704.

Preller et al., "Changes in global and thalamic brain connectivity in LSD-induced altered states of consciousness are attributable to the 5-HT2A receptor", Elife (2018); 7: e35082; 31 pages. doi: 10.7554/eLife.35082.

Preller et al., "The fabric of meaning and subjective effects in LSD-induced states depend on serotonin 2A receptor activation", Current Biology (2017); 27(3): 451-457. doi: 10.1016/j.cub.2016.12.030. Epub Jan. 26, 2017.

Psychiatric University Hospital, Zurich, "The Role of 5-HT2A Receptor in the Perception of Self and Personal Meaning in Healthy Volunteers" ClinicalTrials.gov ID NCT02451072, version 3, Jan. 29, 2016, 10 pages.

Ramaekers et al., "A low dose of lysergic acid diethylamide decreases pain perception in healthy volunteers", Journal of Psychopharmacology (2021); 35: 398-405. doi: 10.1177/0269881120940937. Epub Aug. 25, 2020.

Rasmussen et al., "Effect of hallucinogens on spontaneous and sensory-evoked locus coeruleus unit activity in the rat: reversal by selective 5-HT2 antagonists", Brain Research (1986); 385(2): 395-400. doi: 10.1016/0006-8993(86)91090-5.

Reissig et al., "The 5-HT1A receptor and the stimulus effects of LSD in the rat", Psychopharmacology (2005); 182: 197-204. doi: 10.1007/s00213-005-0068-6. Epub Oct. 19, 2005.

Rickli et al., "Receptor interaction profiles of novel psychoactive tryptamines compared with classic hallucinogens", European Neuropsychopharmacology (2016); 26: 1327-1337. doi: 10.1016/j.euroneuro.2016.05.001. Epub May 20, 2016.

Rigsbee et al., "Polymorph Investigation of Lysergic Acid Diethylamide (LSD) D-Tartrate", Triclinic Labs Scientific Report (Dec. 28, 2021); 43 pages.

Rootman et al., "Psilocybin microdosers demonstrate greater observed improvements in mood and mental health at one month relative to non-microdosing controls", Scientific Reports (2022); 12(1): 11091; 10 pages. doi: 10.1038/s41598-022-14512-3.

Sato et al., "LSD in pregnancy: chromosomal effects", Life Sciences (1971); 10(13): 773-779. doi: 10.1016/0024-3205(71)90209-8.

Savage et al., "Residential psychedelic (LSD) therapy for the narcotic addict. A controlled study", Archives General Psychiatry (1973); 28(6): 808-814. doi: 10.1001/archpsyc.1973.01750360040005.

Schindler et al.,"Indoleamine Hallucinogens in Cluster Headache: Results of the Clusterbusters Medication Use Survey", Journal of Psychoactive Drugs (2015); 47(5): 372-381. doi: 10.1080/02791072.2015.1107664. Epub Nov. 23, 2015.

Schlag et al., "Adverse effects of psychedelics: From anecdotes and misinformation to systematic science", Journal of Psychopharmacology (Mar. 2022); 36(3): 258-272. doi: 10.1177/02698811211069100. Epub Feb. 2, 2022.

(56)　　　　　References Cited

OTHER PUBLICATIONS

Schmid et al., "Acute Effects of Lysergic Acid Diethylamide in Healthy Subjects", Biological Psychiatry (2015); 78(8): 544-553. doi: 10.1016/j.biopsych.2014.11.015. Epub Nov. 29, 2014.

Schmid et al., "Long-lasting subjective effects of LSD in normal subjects", Psychopharmacology (Berl) (2018); 235(2): 535-545. doi: 10.1007/s00213-017-4733- 3. Epub Sep. 16, 2017.

Scully. "A Sketch of the Early History of Underground LSD Manufacturing", In Breaking Convention 2013 event; University of Greenwich (2013); 7 pages.

Seeman et al., "Dopamine D2high receptors stimulated by phencyclidines, lysergic acid diethylamide, salvinorin A, and modafinil", Synapse (2009); 63(8): 698-704. doi: 10.1002/syn.20647.

Seeman et al., "Dopamine receptor contribution to the action of PCP, LSD and ketamine psychotomimetics", Molecular Psychiatry (2005); 10(9): 877-883. doi: 10.1038/sj.mp.4001682.

Sessa. "The pharmacology of LSD: A critical review", The British Journal of Psychiatry (2011); 199(3): 258-259. Abstract Only.

Sewell et al., "Response of cluster headache to psilocybin and LSD", Neurology (2006); 66(12): 1920-1922. doi: 10.1212/01.wnl. 0000219761.05466.43.

Shear et al., "Reliability and validity of a structured interview guide for the Hamilton Anxiety Rating Scale (SIGH-A)", Depress Anxiety (2001); 13(4): 166-78.

Sheehan et al., "Assessing treatment effects in clinical trials with the Discan metric of the Sheehan Disability Scale", International Clinical Psychopharmacology (2008); 23(2): 70-83. doi: 10.1097/YIC. 0b013e3282f2b4d6.

Sheehan et al., "The Mini-International Neuropsychiatric Interview (M.I.N.I.): the development and validation of a structured diagnostic psychiatric interview for DSM-IV and ICD-10", The Journal of Clinical Psychiatry (1998); 59(Suppl 20): 22-33.

Shulgin et al.; "PIHKAL: A Chemical Love Story," Transform Press, Berkeley, CA (1991): 453-923; 239 pages.

Siddik et al., "The fate of lysergic acid di[14C]ethylamide ([14C]LSD) in the rat", Biochemical Society Transactions (1975); 3(2): 290-292.

Siddik et al., "The fate of lysergic acid di[14C]ethylamide ([14C]LSD) in the rat, guinea pig and rhesus monkey and of [14C]iso-LSD in rat", Biochemical Pharmacology (1979); 28(20): 3093-3101.

Siddik et al., "The metabolism of lysergic acid DI[14C]-ethylamide ([14C]LSD) in the isolated perfused rat liver", Biochemical Pharmacology (1979); 28(20): 3081-3091.

Singh et al., "Chromosomal aberrations induced in barley by LSD", Science (Jul. 31, 1970); 169: 491-492. doi: 10.1126/science.169. 3944.491.

Sinton et al., "The effectiveness of different isomers of octanol as blockers of harmaline-induced tremor", Pflügers Archiv: European Journal of Physiology (1989); 414: 31-36. doi: 10.1007/BF00585623.

Skakkebaek et al., "Studies on meiotic chromosomes and spermatozoan heads in mice treated with LSD", Journal of Reproduction and Fertility (1970); 22: 141-144. doi: 10.1530/jrf.0.0220141.

Smith et al., "141. The alkaloids of ergot. Part V. The nature of ergine", Journal of the Chemical Society (Resumed) (1934): 674-675.

Smith et al., "311. The alkaloids of ergot. Part VII. iso Ergine and iso lysergic acids", Journal of the Chemical Society (Resumed) (1936): 1440-1444.

Smith. "Gilles De La Tourette Syndrome Treated with LSD", Irish Journal of Medical Science (Jun. 1969); 2(6): 269-271. doi: 10.1007/BF02955387.

Snyder et al., "Regional Localization of lysergic acid diethylamide in monkey brain", Nature (1966); 209(5028): 1093-1095. doi: 10.1038/2091093a0.

Stachulski et al., "Stereochemical and NMR Reassignment of 6-Norlylsergic Acid Diethylamide and 6-Nor-6-allyllysergic Acid Diethylamide", Journal of Chemical Research (1996); S1: 30-31.

Stein. "Etifoxine versus alprazolam for the treatment of adjustment disorder with anxiety: a randomized controlled trial", Advances in Therapy (2015); 32(1): 57-68. doi: 10.1007/s12325-015-0176-6. Epub Jan. 27, 2015.

Stein. "Pharmacotherapy of adjustment disorder: A review", World Journal of Biological Psychiatry (2018); 19(sup1): S46-S52. doi: 10.1080/15622975.2018.1492736.

Steuer et al., "Development and validation of an ultra-fast and sensitive microflow liquid chromatography-tandem mass spectrometry (MFLC-MS/MS) method for quantification of LSD and its metabolites in plasma and application to a controlled LSD administration study in humans", Drug Test Analysis (2017); 9(5): 788-797. doi: 10.1002/dta.2042. Epub Aug. 10, 2016.

Stocco et al., "The Molecular Control of Corpus Luteum Formation, Function, and Regression", Endocrine Reviews (Feb. 2007); 28(1): 117-149. doi: 10.1210/er.2006-0022. Epub Oct. 31, 2006.

Stoll et al., "Amide der stereoisomeren Lysergsäuren und Dihydrolysergsäuren. 38. Mitteilung über Mutterkornalkaloide", Helvetica Chimica Acta (1955); 38(2): 421-433; 26 pages with English machine translation.

Stoll et al., "Über die Stereochemie der Lysergsäuren und der Dihydro-lysergsäuren. 37. Mitteilung über Mutterkornalkaloide", Helvetica Chimica Acta (1954); 37(7): 2039-2057; 19 pages with English summary.

Stoll et al., "Distribution and fate of14C-labeled lysergic acid diethylamide (LSD 25) in the animal body", Experientia (1955); 11(10): 396-397. doi: 10.1007/BF02158503.

Stoll et al., "Partialsynthese von alkaloiden vom typus des ergobasins. (6. Mitteilung über Mutterkornalkaloide)", Helvetica Chimica Acta (1943); 26(3): 944-965; 48 pages with English machine translation.

Stoll et al., "Uber die Synthese von 14C-Diathylamin und 14C-Lysergsaure-diathylamid", Helvetica Chimica Acta (1954); 37: 820-824; 10 pages with English Machine Translation.

Strajhar et al., "Acute effects of lysergic acid diethylamide on circulating steroid levels in healthy subjects", Journal of Neuroendocrinology (2016); 28: 12374; 13 pages. doi: 10.1111/jne. 12374.

Strassman et al., "Differential tolerance to biological and subjective effects of four closely spaced doses of N, N-dimethyltryptamine in humans", Biological Psychiatry (1996); 39(9): 784-795. doi: 10.1016/0006-3223(95)00200-6.

Studerus et al., "Psychometric evaluation of the altered states of consciousness rating scale (OAV)", PLoS One (2010); 5(8): e12412; 19 pages. doi: 10.1371/journal.pone.0012412. P.

Sturelid et al., "Lysergic acid diethylamide and chromosome breakage", Hereditas (1969); 62(1): 259-262. doi: 10.1111/j.1601-5223. 1969.tb02233.x.

Tadini. "Development of electrochemical sensors for the detection voltammetric analysis of MDMA in samples of forensic interest", Dissertation presented to the Faculty of Philosophy, Sciences and Letters of Ribeirão Preto from the University of São Paulo, as part of the requirements for obtaining the Master's degree in Sciences, Area: Chemistry, University of Sao Paulo, Faculty of Philosophy, Sciences and Letters of Ribeirão Preto, Department of Chemistry, Postgraduate Program in Chemistry (2016); 200 pages with English translation.

Tagliazucchi et al., "Increased global functional connectivity correlates with LSD-induced ego dissolution", Current Biology (2016); 26: 1043-1050. doi: 10.1016/j.cub.2016.02.010. Epub Apr. 13, 2016.

Taschwer et al., "Chiral separation of cathinone and amphetamine derivatives by HPLC/UV using sulfated B-Cyclodextrin as chiral Mobile phase additive", Chirality (2014); 26(8): 411-418. doi: 10.1002/chir.22341. Epub Jun. 9, 2014.

Terhune et al., "A placebo-controlled investigation of synaesthesia-like experiences under LSD", Neuropsychologia (2016); 88: 28-34. doi: 10.1016/j.neuropsychologia.2016.04.005. Epub Apr. 5, 2016.

Titeler et al., "Radioligand binding evidence implicates the brain 5 HT2 receptor as a site of action for LSD and phenylisopropylamine hallucinogens", Psychopharmacology (Berl). (1988); 94: 213-216. doi: 10.1007/BF00176847.

(56)  References Cited

OTHER PUBLICATIONS

Trulson et al., "Dissociations between the effects of hallucinogenic drugs on behavior and raphe unit activity in freely moving cats", Brain Research (1981); 215: 275-293. doi: 10.1016/0006-8993(81)90507-2.

Uhle. "Amino Derivatives of 5-KETO-1, 3, 4, 5-TETRAHYDROBENZ [cd] INDOLE1", Journal of the American Chemical Society (1951); 73(5): 2402-2403.

University Hospital, Basel, Switzerland, "Acute Dose-dependent Effects of DMT in Healthy Subjects (DMT DR)" ClinicalTrials.gov ID NCT05384678, version 1, May 17, 2022, 13 pages.

University Hospital, Basel, Switzerland, "Comparative Acute Effects of LSD, Psilocybin and Mescaline (LPM)" ClinicalTrials.gov ID NCT04227756, version 3, May 27, 2020 12 pages.

University Hospital, Basel, Switzerland, "Comparative Acute Effects of LSD, Psilocybin and Mescaline (LPM)" ClinicalTrials.gov ID NCT04227756, version 4, Aug. 17, 2021, 13 pages.

University Hospital, Basel, Switzerland, "Comparative Acute Effects of LSD, Psilocybin and Mescaline (LPM)" ClinicalTrials.gov ID NCT04227756, version 6, Mar. 30, 2022, 12 pages.

University Hospital, Basel, Switzerland, "Direct Comparison of Altered States of Consciousness Induced by LSD and Psilocybin (LSD-psilo)" ClinicalTrials.gov ID NCT03604744, version 8, Apr. 26, 2021, 11 pages.

University Hospital, Basel, Switzerland, "Effect of Ketanserin After LSD Administration (L-Ket)" ClinicalTrials.gov ID NCT04558294, version 2, Oct. 26, 2020, 13 pages.

University Hospital, Basel, Switzerland, "Effect of Ketanserin After LSD Administration (L-Ket)" ClinicalTrials.gov ID NCT04558294, version 3, Oct. 20, 2021, 13 pages.

University Hospital, Basel, Switzerland, "Effects of MDMA Co-administration on the Response to LSD in Healthy Subjects (LSD-MDMA)" ClinicalTrials.gov ID NCT04516902, version 2, Jan. 25, 2021, 13 pages.

University Hospital, Basel, Switzerland, "Effects of MDMA Co-administration on the Response to LSD in Healthy Subjects (LSD-MDMA)" ClinicalTrials.gov ID NCT04516902, version 3, Sep. 6, 2021, 13 pages.

University Hospital, Basel, Switzerland, "Effects of SERT Inhibition on the Subjective Response to LSD in Healthy Subjects (SERT-LSD)" ClinicalTrials.gov ID NCT05175430, version 1, Dec. 14, 2021, 13 pages.

University Hospital, Basel, Switzerland, "LSD Base and LSD Tartrate Bioequivalence and Bioavailability in Healthy Subjects (LSD-Bio)" ClinicalTrials.gov ID NCT04865653, version 1, Apr. 26, 2021, 14 pages.

University Hospital, Basel, Switzerland, "LSD Base and LSD Tartrate Bioequivalence and Bioavailability in Healthy Subjects (LSD-Bio)" ClinicalTrials.gov ID NCT04865653, version 3, Mar. 20, 2022, 14 pages.

University Hospital, Basel, Switzerland, "LSD Therapy for Persons Suffering From Major Depression (LAD)" ClinicalTrials.gov ID NCT03866252, version 10, May 24, 2022, 14 pages.

University Hospital, Basel, Switzerland, "LSD Therapy for Persons Suffering From Major Depression (LAD)" ClinicalTrials.gov ID NCT03866252, version 8, Feb. 8, 2021, 14 pages.

University Hospital, Basel, Switzerland, "LSD Treatment in Persons Suffering From Anxiety Symptoms in Severe Somatic Diseases or in Psychiatric Anxiety Disorders (LSD-assist)" ClinicalTrials.gov ID NCT03153579, version 7, Dec. 21, 2021, 12 pages.

University Hospital, Basel, Switzerland, "LSD Treatment in Persons Suffering From Anxiety Symptoms in Severe Somatic Diseases or in Psychiatric Anxiety Disorders (LSD-assist)" ClinicalTrials.gov ID NCT03153579, version 9, Mar. 12, 2020, 11 pages.

University Hospital, Basel, Switzerland, "Lysergic Acid Diethylamide (LSD) as Treatment for Cluster Headache (LCH)" ClinicalTrials.gov ID NCT03781128, version 4, Apr. 19, 2021, 14 pages.

University Hospital, Basel, Switzerland, "Lysergic Acid Diethylamide (LSD) as Treatment for Cluster Headache (LCH)" ClinicalTrials.gov ID NCT03781128, version 5, May 4, 2022, 14 pages.

University Hospital, Basel, Switzerland, "Neuronal Correlates of Altered States of Consciousness (5HT2A-fMRI)" ClinicalTrials.gov ID NCT02308969, version 4, Sep. 24, 2015, 9 pages.

University Hospital, Basel, Switzerland, "Psychological, Physiological, Endocrine, and Pharmacokinetic Effects of LSD in a Controlled Study" ClinicalTrials.gov ID NCT01878942, version 7, Jan. 20, 2016, 10 pages.

University Hospital, Basel, Switzerland, "Role of Dopamine, Serotonin and 5-HT2A Receptors in Emotion Processing (LAM)" ClinicalTrials.gov ID NCT03019822, version 6, Oct. 12, 2018, 12 pages.

University Hospital, Basel, Switzerland, "Role of the Serotonin 5-HT2A Receptor in LSD-induced Altered States of Consciousness (LDR-Study) (LDR)" ClinicalTrials.gov ID NCT03321136, version 9, Aug. 26, 2019, 15 pages.

University Hospital, Basel, Switzerland, "Role of the Serotonin 5-HT2A Receptor in Mescaline-induced Altered States of Consciousness (MDR)" ClinicalTrials.gov ID NCT04849013, version 2, Apr. 19, 2021, 15 pages.

University Hospital, Basel, Switzerland, "Role of the Serotonin 5-HT2A Receptor in Mescaline-induced Altered States of Consciousness (MDR)" ClinicalTrials.gov ID NCT04849013, version 3, Aug. 17, 2021, 15 pages.

University of Chicago, "Mood Effects of Serotonin Agonists" ClinicalTrials.gov ID NCT03790358, version 1, Dec. 28, 2018, 9 pages.

U'Prichard. "Binding characteristics of a radiolabeled agonist and antagonist at central nervous system alpha noradrenergic receptors." Molecular Pharmacology, 1977; 13(3): 454-473.

U.S. Department of Health and Human Services Food and Drug Administration Center for Drug Evaluation and Research. "Guidance for Industry: Estimated the Maximum Safe Starting Dose in Initial Clinical Trials for Therapeutics in Adult Health Volunteers", (CDER) Pharmacology and Toxicology (Jul. 2005); 30 pages.

U.S. Department of Veterans Affairs. "How Common Is PTSD in Adults?", National Center for PTSD (Feb. 3, 2023) [online] https://web.archive.org/web/20230203040213/https://www.ptsd.va.gov/understand/common/common_adults.asp (Access Date: Feb. 11, 2024); 2 pages.

U.S. Appl. No. 18/750,991, filed Jun. 21, 2024, by Trachsel et al.

U.S. Appl. No. 19/020,135, filed Jan. 14, 2025, by Liechti et al.

Van Went. "Mutagenicity testing of 3 hallucinogens: LSD, psilocybin and ‡ 9-THC using the micronucleus test", Experientia (1978); 34(3): 324-325. doi: 10.1007/BF01923013.

Verstraete et al., "2-oxo-3-hydroxy-LSD: An important LSD metabolite?", Acta Clinica Belgica (1999); 53(Suppl1): 94-96.

Vizeli et al., "Genetic influence of CYP2D6 on pharmacokinetics and acute subjective effects of LSD in a pooled analysis", Scientific Reports (2021); 11(1): 10851; 9 pages. doi: 10.1038/s41598-021-90343-y.

Wacker et al., "Crystal structure of an LSD-bound human serotonin receptor", Cell (2017); 168: 377-389. doi: 10.1016/j.cell.2016.12.033.

Waghorn et al., "Disability, employment and work performance among people with ICD-10 anxiety disorders", Australian & New Zealand Journal of Psychiatry (2005); 39(1-2): 55-66. doi: 10.1080/j.1440-1614.2005.01510.x.

Wan et al., "Estimation of symptom-free days in generalized anxiety disorder", Current Medical Research and Opinion (2006); 22(3): 587-591. doi: 10.1185/030079906X96245.

Warkany et al., "Lysergic acid diethylamide (LSD): No. teratogenicity in rats", Science (1968); 159: 731-732. doi: 10.1126/science.159.3816.731.

Watts et al., "LSD and structural analogs: pharmacological evaluation at D1 dopamine receptors", Psychopharmacology (Berl) (1995); 118: 401-409. doi: 10.1007/BF02245940.

Wing et al., "5HT-2 mediation of acute behavioral effects of hallucinogens in rats", Psychopharmacology (1990); 100: 417-425. doi: 10.1007/BF02244617.

Winter. "Tolerance to a behavioral effect of lysergic acid diethylamide and cross-tolerance to mescaline in the rat: Absence of a metabolic component", Journal of Pharmacology and Experimental Therapeutics (1971); 178: 625-630.

(56)	References Cited

OTHER PUBLICATIONS

World Health Organization. "Anxiety Disorders", Sep. 27, 2023 [online] https://www.who.int/news-room/fact-sheets/detail/anxiety-disorders (Access Date: Jun. 20, 2024); 5 pages.
Yanakieva et al., "The effects of microdose LSD on time perception: a randomised, double-blind, placebo-controlled trial." Psychopharmacology (2018); 236: 1159-1170. doi: 10.1007/s00213-018-5119-x. Epub Nov. 26, 2018. Erratum in: Psychopharmacology (Berl). Dec. 2020;237(12):3803. doi: 10.1007/s00213-020-05682-x.
Zeiger et al., "Salmonella Mutagenicity tests: III. Results from the testing of 255 chemicals", Molec Mutagen (1987); 9(S9): 1-109.
Carhart-Harris et al. "Psilocybin with psychological support for treatment-resistant depression: an open-label feasibility study." The Lancet Psychiatry. Jul. 2016;3(7):619-627. doi: 10.1016/S2215-0366(16)30065-7.
Dissanayaka et al., "Anxiety rating scales in Parkinson's disease: a critical review updating recent literature." International Psychogeriatrics. Nov. 2015;27(11): 1777-1784. doi: 10.1017/S1041610215000885.
Donzuso et al. The neuroanatomical correlates of anxiety in a healthy population: differences between the State-Trait Anxiety Inventory and the Hamilton Anxiety Rating Scale. Brain and Behavior. Jul. 2014;4(4):504-514. doi: 10.1002/brb3.232.
Hysek et al. "α1-adrenergic receptors contribute to the acute effects of 3, 4-methylenedioxymethamphetamine in humans." Journal of Clinical Psychopharmacology. Oct. 2013;33(5):658-666. doi: 10.1097/JCP.0b013e3182979d32.
Hysek et al. "Carvedilol inhibits the cardiostimulant and thermogenic effects of MDMA in humans." British Journal of Pharmacology. Aug. 2012; 166(8):2277-2288. doi: 10.1111/j.1476-5381.2012.01936.x.
Hysek et al. "Duloxetine inhibits effects of MDMA ("ecstasy") in vitro and in humans in a randomized placebo-controlled laboratory study." PloS One. May 2012;7(5): e36476, 15 pages. doi: 10.1371/journal.pone.0036476.
Hysek et al. "Effects of MDMA alone and after pretreatment with reboxetine, duloxetine, clonidine, carvedilol, and doxazosin on pupillary light reflex." Psychopharmacology. Dec. 2012;224(3):363-376. doi: 10.1007/s00213-012-2761-6.
Hysek et al. "Effects of the α2-adrenergic agonist clonidine on the pharmacodynamics and pharmacokinetics of 3, 4-methylenedioxymethamphetamine in healthy volunteers." The Journal of Pharmacology and Experimental Therapeutics. Feb. 2012;340(2):286-294. doi: 10.1124/jpet.111.188425.
Hysek et al. "MDMA enhances emotional empathy and prosocial behavior." Social Cognitive and Affective Neuroscience. Nov. 2014;9(11):1645-1652. doi: 10.1093/scan/nst161.
Hysek et al. "MDMA enhances "mind reading" of positive emotions and impairs "mind reading" of negative emotions." Psychopharmacology. Jul. 2012;222(2):293-302. doi: 10.1007/s00213-012-2645-9.
Hysek et al. "Pharmacokinetic and pharmacodynamic effects of methylphenidate and MDMA administered alone or in combination." International Journal of Neuropsychopharmacology. Mar. 2014; 17(3):371-381. doi: 10.1017/S1461145713001132.
Hysek et al. "The norepinephrine transporter inhibitor reboxetine reduces stimulant effects of MDMA ("ecstasy") in humans." Clinical Pharmacology & Therapeutics. Aug. 2011;90(2):246-255. doi: 10.1038/clpt.2011.78.
Jacobsen et al. "Rapid and Durable Response to a Single Dose of MM120 (Lysergide) in Generalized Anxiety Disorder: A Dose Optimization Study." [poster] Interdisciplinary Conference on Psychedelic Research, Jun. 6-8, 2024, Haarlem, Netherlands; 1 page.
Karlin et al. "MM120 (Lysergide) for GAD: Results From Mindmed's Phase 2 Trial", 2024 ASCP Annual Meeting, Innovations in Clinical Research: Broadening Clinical Trial Methods, Endpoints and Goals, Abstract Book, Miami Beach, Florida (May 28-31, 2024); pp. 42-43; 3 pages total.
Liechti et al. "Acute psychological and physiological effects of MDMA ("Ecstasy") after haloperidol pretreatment in healthy humans."
European Neuropsychopharmacology. Jul. 2000; 10(4):289-295. doi: 10.1016/s0924-977x(00)00086-9.
Liechti et al. "Acute psychological effects of 3, 4-methylenedioxymethamphetamine (MDMA, "Ecstasy") are attenuated by the serotonin uptake inhibitor citalopram." Neuropsychopharmacology. May 2000;22(5):513-521. doi: 10.1016/S0893-133X(99)00148-7.
Liechti et al. "Gender differences in the subjective effects of MDMA." Psychopharmacology. Mar. 2001; 154(2):161-168. doi: 10.1007/s002130000648.
Liechti et al. "Psychological and physiological effects of MDMA ("Ecstasy") after pretreatment with the 5-HT2 antagonist ketanserin in healthy humans." Neuropsychopharmacology. Oct. 2000;23(4):396-404. doi: 10.1016/S0893-133X(00)00126-3.
Liechti et al. "The serotonin uptake inhibitor citalopram reduces acute cardiovascular and vegetative effects of 3, 4-methylenedioxymethamphetamine ('Ecstasy') in healthy volunteers." Journal of Psychopharmacology. May 2000; 14(3):269-274. doi: 10.1177/026988110001400313.
Liechti et al. "Which neuroreceptors mediate the subjective effects of MDMA in humans? A summary of mechanistic studies." Human Psychopharmacology: Clinical and Experimental. Dec. 2001;16(8):589-598. doi: 10.1002/hup.348.
Non-Final Office Action for U.S. Appl. No. 18/197,892, by Barrow, Robert, et al., mailed on Sep. 9, 2025, 9 pages.
Rickels et al. "Paroxetine treatment of generalized anxiety disorder: a double-blind, placebo-controlled study." American Journal of Psychiatry. Apr. 2003; 160(4):749-756.
Rickli et al. Receptor interaction profiles of novel N-2-methoxybenzyl (NBOMe) derivatives of 2, 5-dimethoxy-substituted phenethylamines (2C drugs). Neuropharmacology. Dec. 2015;99:546-553.
Ringeisen et al. "Mental and Substance Use Disorders Prevalence Study (MDPS): Findings Report." RTI International. 2023, 77 pages.
Rodriguiz et al. "LSD-stimulated behaviors in mice require β-arrestin 2 but not β-arrestin 1." Scientific Reports. Sep. 11, 2021(1):17690, 14 pages.
Romano et al. "Intrahippocampal LSD accelerates learning and desensitizes the 5-HT$_{2A}$ receptor in the rabbit." Psychopharmacology. Oct. 2010;212(3):441-448.
Ross et al. "Rapid and sustained symptom reduction following psilocybin treatment for anxiety and depression in patients with life-threatening cancer: a randomized controlled trial." Journal of Psychopharmacology. Dec. 2016;30(12):1165-1180. doi: 10.1177/0269881116675512.
Rothlin E. "Metabolism of lysergic acid diethylamide." Nature. Dec. 22, 1956;178(4547):1400-1401.
Rothlin et al. "Pharmacology of LSD-25. Lysergic acid diethylamide and mescaline in experimental psychiatry." Grune & Stratton, New York. 1956, pp. 1-7, 9 total pages.
Roux et al. "LSD: No teratogenic action in rats, mice, and hamsters." Science. Aug. 1970; 169(3945): 588-599.
Ruscio et al. "Cross-sectional comparison of the epidemiology of DSM-5 generalized anxiety disorder across the globe." JAMA Psychiatry. May 2017;74(5):465-475.
Rynn et al. "Efficacy and safety of duloxetine in the treatment of generalized anxiety disorder: a flexible-dose, progressive-titration, placebo-controlled trial." Depression and Anxiety. Mar. 2008;25(3):182-189.
Sanders-Bush et al. "Lysergic acid diethylamide and 2, 5-dimethoxy-4-methylamphetamine are partial agonists at serotonin receptors linked to phosphoinositide hydrolysis." The Journal of Pharmacology and Experimental Therapeutics. Sep. 1988;246(3):924-928.
Schell D. "Defying Industry Setbacks, MindMed Advances Psychedelic to Phase 0001." Clinical Leader (Jul. 17, 2024) [online] https://www.clinicalleader.com/doc/defying-industry-setbacks-mindmed-advances-psychedelic-to-phase-0001; 2 pages.
Schmid et al. "CYP2D6 function moderates the pharmacokinetics and pharmacodynamics of 3, 4-methylene-dioxymethamphetamine in a controlled study in healthy individuals." Pharmacogenetics and Genomics. Aug. 2016;26(8):397-401. doi: 10.1097/FPC.0000000000000231.

(56) References Cited

OTHER PUBLICATIONS

Schmid et al. "Differential effects of MDMA and methylphenidate on social cognition." Journal of Psychopharmacology. Sep. 2014;28(9):847-856. doi: 10.1177/0269881114542454.

Schmid et al. "Interactions between bupropion and 3,4-methylenedioxymethamphetamine in healthy subjects." The Journal of Pharmacology and Experimental Therapeutics. Apr. 2015;353(1):102-111. doi: 10.1124/jpet.114.222356.

Shulgin et al. "TIHKAL: The Continuation." Berkeley: Transform Press. 1997: pp. 159-191, 346-383, 592-611, 728-773; 152 total pages.

Simmler et al. "Sex differences in the effects of MDMA (ecstasy) on plasma copeptin in healthy subjects." The Journal of Clinical Endocrinology & Metabolism. Sep. 2011;96(9):2844-2850. doi: 10.1210/jc.2011-1143.

Studerus et al. "Prediction of MDMA response in healthy humans: a pooled analysis of placebo-controlled studies." Journal of Psychopharmacology. May 2021;35(5):556-565. doi: 10.1177/0269881121998322.

Vizeli et al. "Pharmacogenetics of ecstasy: CYP1A2, CYP2C19, and CYP2B6 polymorphisms moderate pharmacokinetics of MDMA in healthy subjects." European Neuropsychopharmacology. Mar. 2017;27(3):232-238. doi: 10.1016/j.euroneuro.2017.01.008.

Vizeli et al. "Role of serotonin transporter and receptor gene variations in the acute effects of MDMA in healthy subjects." ACS Chemical Neuroscience. Jul. 2019;10(7):3120-3131. doi: 10.1021/acschemneuro.8b00590.

Vizeli et al. "Safety pharmacology of acute MDMA administration in healthy subjects." Journal of Psychopharmacology. May 2017;31(5):576-588. doi: 10.1177/0269881117691569.

Vollenweider et al. "Psilocybin induces schizophrenia-like psychosis in humans via a serotonin-2 agonist action." Neuroreport. Dec. 1998;9(17):3897-3902. doi: 10.1097/00001756-199812010-00024.

Vollenweider et al. "Psychological and cardiovascular effects and short-term sequelae of MDMA ("ecstasy") in MDMA-naïve healthy volunteers." Neuropsychopharmacology. Oct. 1998; 19(4):241-251. doi: 10.1016/S0893-133X(98)00013-X.

Arrnbrecht et al. "Economic and humanistic burden associated with depression and anxiety among adults with non-communicable chronic diseases (NCCDs) in the United States." Journal of Multidisciplinary Healthcare. Apr. 2021:887-896. doi:10.2147/JMDH.5280200.

Baldwin et al. "Evidence-based pharmacological treatment of generalized anxiety disorder." International Journal of Neuropsychopharmacology. Jun. 2011;14(5):697-710. doi: 10.1017/S1461145710001434.

Bang et al. "Assessment of blinding in clinical trials." Controlled Clinical Trials. Apr. 2004;25(2):143-156. doi: 10.1016/j.cct2003.10.016.

Barrera et al. "Quality of life impairment in generalized anxiety disorder, social phobia, and panic disorder." Journal of Anxiety Disorders. Dec. 2009;23(8):1086-1090. doi: 10.1016/j.janxdis.2009.07.011.

Carl et al. "Psychological and pharmacological treatments for generalized anxiety disorder (GAD): a meta-analysis of randomized controlled trials." Cognitive Behaviour Therapy. Jan. 2020;49(1):1-21. doi:10.1080/16S06073.2018.1560358.

Clayton et al. "The Changes in Sexual Functioning Questionnaire (CSFQ): Development, Reliability and Validity." Psychopharmacology Bulletin. Jan. 1997;33(4):731-745.

Cohen et al. "Placebo response mitigation with a participant-focused psychoeducational procedure: a randomized, single-blind, all placebo study in major depressive and psychotic disorders." Neuropsychopharmacology. Mar. 2021;46(4):844-850. doi: 10.1038/s41386-020-00911-5.

Daly et al. "Efficacy and safety of intranasal esketamine adjunctive to oral antidepressant therapy in treatment-resistant depression: a randomized clinical trial." JAMA Psychiatry. Feb. 2018;75(2):139-148. doi: 10.1001/jamapsychiatry.2017.3739.

Das et al. "Lysergic acid diethylamide: a drug of 'use'." Therapeutic Advances in Psychopharmacology. Jun. 2016;6(3):214-228. doi: 10.1177/2045125316640440.

Desseilles et al. "Massachusetts General Hospital SAFER criteria for clinical trials and research." Harvard Review of Psychiatry. Sep. 2013;21(5):269-274. doi: 10.1097/HRP.0b013e3182a75cc7.

Eli Lilly "FDA Approves Cymbalta for Treatment of Generalized Anxiety Disorder." Eli Lilly [news release]. Feb. 26, 2007; 3 pages. [retrieved online] [retrieved on Oct. 15, 2025]. URL: https://investor.lilly.com/static-files/499f0aa3-281f-49f4-9655-049aae179593.

Garakani et al. "Pharmacotherapy of Anxiety Disorders: Current and Emerging Treatment Options." Focus, American Psychiatric Publishing; Jun. 2021; 19(2):222-242. doi: 10.1176/appi.focus.19203.

Hamilton MA. "The assessment of anxiety states by rating." British Journal of Medical Psychology. Mar. 2, 1959;32:81-82.

Jauhar et al. "Esketamine for treatment resistant depression." BMJ. Sep. 2019;366:I5572, 2 pages. doi: 10.1136/bmj.I5572.

Kaiser et al. "Unraveling the comorbidity of depression and anxiety in a large inpatient sample: Network analysis to examine bridge symptoms." Depression and Anxiety. Mar. 2021;38(3):307-317. doi: 10.1002/da.23136.

Keller et al. "Reliability and construct validity of the Changes in Sexual Functioning Questionnaire short-form (CSFQ-14)." Journal of Sex & Marital Therapy. Jan. 2006;32(1):43-52. oi: 10.1080/00926230500232909.

Machado-Vieira et al. "The timing of antidepressant effects: a comparison of diverse pharmacological and somatic treatments." Pharmaceuticals. Jan. 2010;3(1):19- 41. doi: 10.3390/ph3010019.

Matza et al. "Identifying HAM-A cutoffs for mild, moderate, and severe generalized anxiety disorder." International Journal of Methods in Psychiatric Research. Dec. 2010;19(4):223-232. doi: 10.1002/mpr.323.

Mora et al. "Lessons learned from placebo groups in antidepressant trials." Philosophical Transactions of the Royal Society B: Biological Sciences. Jun. 2011;366(1572):1879-1888. doi: 10.1098/rstb.2010.0394.

Morean et al. "The drug effects questionnaire: psychometric support across three drug types." Psychopharmacology. May 2013;227(1):177-192. doi: 10.1007/s00213-012-2954-z.

Muthukumaraswamy et al. "Blinding and expectancy confounds in psychedelic randomized controlled trials." Expert Review of Clinical Pharmacology. Sep. 2021;14(9):1133-1152. doi: 10.1080/17512433.2021.1933434.

Newman et al. "Worry and generalized anxiety disorder: a review and theoretical synthesis of evidence on nature, etiology, mechanisms, and treatment." Annual Review of Clinical Psychology. Mar. 2013;9(1):275-297. doi: 10.1146/annurev-clinpsy-050212-185544.

Patriquin et al. "The neurobiological mechanisms of generalized anxiety disorder and chronic stress." Chronic Stress. May 2017;1:1-10. doi: 10.1177/2470547017703993.

Reilly et al. "The validity and reproducibility of a work productivity and activity impairment instrument." Pharmacoeconomics. Nov. 1993;4(5):353-365. doi: 10.2165/00019053-199304050-00006.

Robinson et al. "Single Treatment with MM120 (Lysergide) in Generalized Anxiety Disorder." JAMA. Sep. 2025:E1-E15. doi: 10.1001/jama.2025.13481.

Strawn et al. "Pharmacotherapy for generalized anxiety disorder in adult and pediatric patients: an evidence-based treatment review." Expert Opinion on Pharmacotherapy. Jul. 2018;19(10):1057-1070. doi: 10.1080/146S6S66.2018.1491966.

Williams et al. "Development and reliability of a structured interview guide for the Montgomery Åsberg Depression Rating Scale (SIGMA)." Br J Psychiatry. 2008;192(1):52-58. doi: 10.1192/bjp.bp.106.032532.

Erowid, Ecstasy May Relieve Parkinson's Symptoms, Retrieved from Apr. 2, 2008, Originally postedÂ 2003, https://web.archive.org/web/20080402083142/http://www.erowid.org/chemicals/mdma/mdma_research3.shtml.†

Morton, Ecstasy: pharmacology and neurotoxicity, vol. 5(1) pp. 79-86, Current Opinion in Pharmacology. Published Dec. 13, 2004.†

(56)     References Cited

OTHER PUBLICATIONS

Rutten, Anxiety in Parkinson's disease: Symptom dimensions and overlap with depression and autonomic failure, vol. 21(3) pp. 189-193, Parkinsonism & Related Disorders. Published Dec. 9, 2014.†
BBC News Health, Ecstasy Relieves Parkinsons Disease, Retrieved from Jul. 18, 2009, Originally posted 2001, https://web.archive.org/web/20090718174357/http://news.bbc.co.uk/2/hi/health/1169980.stm.†

* cited by examiner
† cited by third party

MOVEMENT DISORDERS

CROSS-REFERENCE

This application claims the benefit of U.S. Provisional Application No. 63/183,771, filed May 4, 2021, the contents of which are incorporated herein by reference in their entirety.

BACKGROUND OF THE INVENTION

1. Technical Field

The present invention relates to compositions and methods for treatments of movement disorders. More specifically, the present invention relates to methods of treating movement disorders with psychedelics.

2. Background Art

Tremors are involuntary, rhythmic, and oscillatory movement of a body part and are the most common movement disorder. They are caused by alternating or synchronous contractions of antagonistic muscles. Tremors can occur when the body is in a rest state (the body part is fully supported, relaxed, or not voluntarily activated) or in an action state (during voluntary movement, during a particular posture, or during muscle contraction against a stationary object).

Parkinson's disease is a common rest tremor and also causes stiffness, slow decreased movement, and imbalance. Rest tremor is usually treated with antiparkinson agents such as anticholinergic drugs, amantadine, dopamine agonists, levodopa, or zonisamide.

Essential tremor (ET) is a common action tremor, and most often affects hands and arms and can also affect the head, voice, face, or trunk. ET is activated by voluntary movement or when the arms are held in a fixed posture against gravity. ET has a strong genetic component and runs in families. 1 percent of the worldwide population suffers from ET and 5 percent of adults over 60 years old. Tremors can be exacerbated due to anxiety, excitement, or other adrenergic stimulation. Action tremors such as ET can be treated with propranolol or primidone as the two primary treatments, or with topiramate, gabapentin, botulinum toxin injections, as well as deep brain stimulation and unilateral thalamotomy. Primidone has acute adverse reactions (sedation, drowsiness, fatigue, depression, nausea, vomiting, ataxia, malaise, dizziness, unsteadiness, confusion, vertigo, and an acute toxic reaction), and propranolol has chronic side effects (lightheadedness, fatigue, impotence, and bradycardia).

Tremors are also a side effect of certain drugs. Drugs that can cause tremors include cancer medicines such as thalidomide and cytarabine, seizure medicines such as valproic acid and sodium valproate, asthma medicines such as theophylline and albuterol, immune suppressing medicines such as cyclosporine and tacrolimus, mood stabilizers such as lithium carbonate, stimulants such as caffeine and amphetamines, antidepressant drugs such as selective serotonin reuptake inhibitors (SSRIs) and tricyclics, heart medicines such as amiodarone, procainamide, and others, certain antibiotics, certain antivirals, such as acyclovir and vidarabine, alcohol, nicotine, certain high blood pressure drugs, epinephrine and norepinephrine, weight loss medicine (tiratricol), too much thyroid medicine (levothyroxine), or tetrabenazine, a medicine to treat excessive movement disorder.

Individuals are embarrassed by this side effect but it will not go away unless they stop taking the drug or dosing can be adjusted.

Psychedelics are substances capable of inducing exceptional subjective effects such as a dream-like alteration of consciousness, affective changes, enhanced introspective abilities, visual imagery, pseudo-hallucinations, synaesthesia, altered temporal and special perception, mystical-type experiences, disembodiment and ego dissolution (Liechti, 2017; Passie, Halpern, Stichtenoth, Emrich & Hintzen, 2008). Psychedelics can be used to assist psychotherapy for many indications including anxiety, depression, addiction, personality disorder and others and can also be used to treat other disorders such as cluster headache and migraine and others (Passie et al., 2008; Hintzen et al., 2010; Nichols, 2016; Liechti, 2017).

There remains a need for an effective treatment for movement disorders.

SUMMARY OF THE INVENTION

The present invention provides for a method of treating movement disorders, by administering an effective amount of a psychedelic to an individual having a movement disorder and treating the movement disorder.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
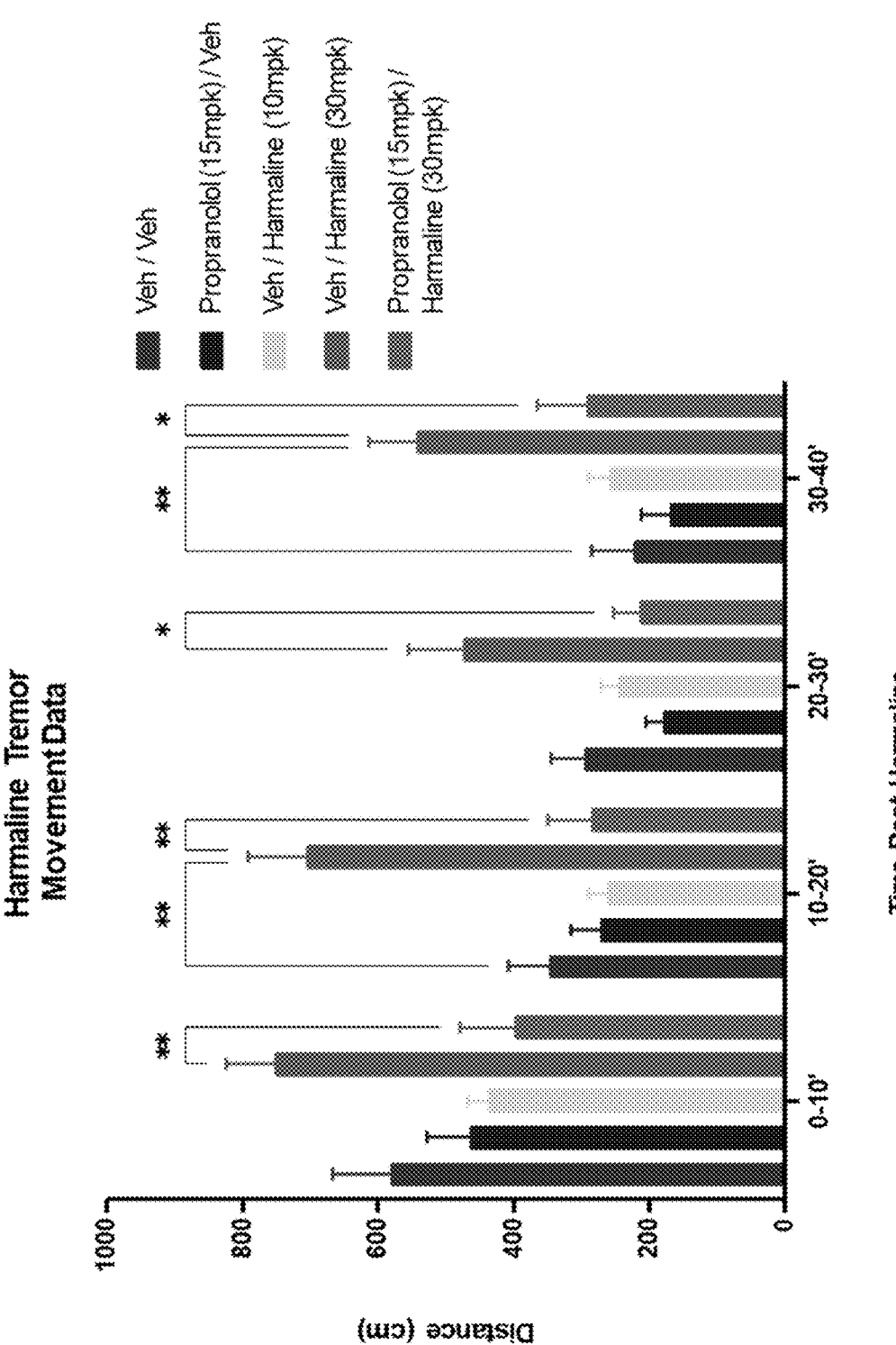
FIG. 1 is a graph of locomotor activity/movement data from a harmaline-induced tremor model in rats.

The present invention provides for a method of treating movement disorders, by administering an effective amount of a psychedelic to an individual having a movement disorder and treating the movement disorder.

"Movement disorder" as used herein, can refer to any neurological condition that results in abnormal increased movements in the body, reduced movements, or slow movements. The movements can be voluntary or involuntary. The movement disorders treated herein can include, but are not limited to, ataxia, cervical dystonia, chorea, dystonia, functional movement disorder, Huntington's disease, multiple system atrophy, myoclonus, Parkinson's disease, Parkinsonism, progressive supranuclear palsy, restless legs syndrome, tardive dyskinesia, Tourette syndrome, tremor (including essential tremor), or Wilson's disease. The movement disorder can be a rest tremor or action tremor. The movement disorder can also be caused by side effects of drugs the individual is taking.

The psychedelics in the present invention can be, but are not limited to, lysergic acid diethylamide (LSD), psilocybin, psilocin, mescaline, 3,4-methylenedioxymethamphetamine (MDMA, including its individual enantiomer forms R-MDMA or S-MDMA), 5-methoxy-N,N-dimethyltryptamine (5-MeO-DMT), dimethyltryptamine (DMT), 2,5-dimethoxy-4-iodoamphetamine (DOI), 2,5-dimethoxy-4-bromo-amphetamie (DOB), salts thereof, tartrates thereof, solvates thereof, isomers thereof, analogs thereof, homologues thereof, or deuterated forms thereof. Preferably, the dose of the psychedelic is one that provides a meaningful clinical effect or can be a dose that is a perceptual dose or subperceptual dose. The psychedelic drug can be administered as a single dose or as repeat doses over multiple days, weeks, months, or years. A dose of 0.05-1 mg (10-1000 µg) can be used of LSD. Psilocybin can be dosed at 1-50 mg, psilocin can be dosed at 1-100 mg, mescaline can be dosed at 10-1000 mg, 5-MeO-DMT can be dosed at 0.2-20 mg, DMT can be dosed at 10-100 mg, DOI can be dosed at 0.1-10 mg, and DOB can be dosed at 0.1-5 mg. Effects of a single dose of the psychedelic drug can last 1-12 hours after administration, and the individual can be supervised by medical personnel such as a psychiatrist during this time. If lower doses are given, medical supervision can be unnecessary.

Mechanistically, psychedelics act as nonspecific serotonin agonists. LSD potently stimulates the $5\text{-HT}_{2A}$ receptor but also $5\text{-HT}_{2B/C}$, $5\text{-HT}_1$ and $D_{1\text{-}3}$ receptors (Rickli et al., 2016). Serotonergic psychedelics have their psychoactive/hallucinogenic effects by agonism at the serotonin $5\text{-HT}_{2A}$ receptor. LSD induces its psychedelic effects in humans primarily via stimulation of the $5\text{-HT}_{2A}$ receptor (Kraehenmann et al., 2017; Preller et al., 2017; Barrett et al., 2018). Psilocybin (3-(2-dimethylaminoethyl)-1H-indol-4-yl] dihydrogen phosphate) is a psychedelic drug that is produced by psilocybin mushrooms, such as, but not limited to, *P. azurescens, P. semilanceata*, and *P. cyanescens*. Psilocin, the active metabolite of psilocybin, inhibits the 5-HT transporter (SERT) whereas LSD stimulates $D_{1\text{-}3}$ receptors but does not interact with the SERT (Rickli et al., 2016). In contrast to LSD, psilocybin and mescaline show no affinity for D2 receptors. The potent dopaminergic receptor agonist properties of LSD have been linked to delayed LSD effects that are possibly distinct from other hallucinogens and possibly more stimulant-like (Mittman et al., 1991; Marona-Lewicka et al., 2005; Marona-Lewicka et al., 2007; Nichols, 2016). LSD and the tryptamines DMT and psilocin are potent agoinsts at serotonin 5-HT1 receptors while other hallucinogens such as mescaline exhibit low potency at this receptor (Rickli et al., 2016). While no clinical studies have clearly documented a role for the 5-HT1 receptor (Strassman, 1996; Nichols, 2016) in the action of psychedelics, differences between substances may exist. SERT inhibition (Rickli et al., 2016) and increases in serotonin by psilocybin may be associated with greater serotonergic toxicity including nausea and vomiting when psilocybin is used compared to other psychedelics with no interaction with the SERT. Mescaline binds in a similar concentration range to $5\text{-HT}_{2A}$, $5\text{-HT}_{1A}$ and adrenergic $\alpha_{2A}$ receptors (Rickli et al., 2016). In treating movement disorders, the effect of the psychedelics can be a CNS effect, direct peripheral effect, or combination of both. As with the treatment of other disorders, there are multiple schools of thought as to how psychedelics exert their effects. There is evidence that they are effective via psychological mechanisms, based in the experience of the direct effects of the drug on 5HT2A receptors. There is also evidence that they have direct neurobiological effects in the brain, and that they enhance whole brain connectivity and introduce a new degree of neuroplasticity in cortical neurons. Further, there is evidence of effect driven by central nervous system binding outside of the brain in addition to peripheral nervous system effects outside of the spinal cord. Though the exact mechanism of action against movement disorders remains not fully specified, it is likely some combination of these putative mechanisms.

In the method of the present invention, treating the movement disorder can include reducing and/or eliminating undesired movement or tremors, or returning any abnormal movement to a normal state. The method can further include reducing anxiety and therefore reducing abnormal movement due to anxiety. The method can further reduce tremors due to side effects of the drugs that the individual is taking.

The compounds of the present invention are administered and dosed in accordance with good medical practice, considering the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that they can be administered as the compound and can be administered alone or as an active ingredient in combination with pharmaceutically acceptable carriers, diluents, adjuvants, and vehicles. The compounds can be administered orally, transcutaneously, subcutaneously or parenterally including sublingual, buccal, inhalation, intravenous, intramuscular, and intranasal administration. The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material not reacting with the active ingredients of the invention.

The doses can be single doses or multiple doses or a continuous dose over a period of several hours, days, weeks, months, or years.

When administering the compound of the present invention orally, it will generally be formulated in an immediate release capsule, immediate release tablet, modified release capsule or tablet (including enteric coatings), solution, or suspension. When administering the compound of the present invention parenterally, it will generally be formulated in a sublingual or buccal orally dissolving tablet, dissolving film, intranasal powder, intranasal solution, inhaled powder, inhaled solution, transdermal patch, transdermal patch with microneedles or other permeation enhancers, or as a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable R-MDMA—25 mg/kg. Dose Frequency: 1x. Study duration: 1 day. Pretreatment time (up to 2 hours): 15 minutes. Number of Groups: 4. Number of animals per group: 10. Total number of animals: 40. The study design is summarized in TABLE 1.

TABLE 1

| GROUP # | TREATMENT | GROUP SIZE | DAYS OF DOSING | DOSE TA/ HARMALINE (MG/KG) | ROUTE TA/ HARMALINE | EVALUATIONS/ ENDPOINTS |
|---|---|---|---|---|---|---|
| 1 | Vehicle/Saline | 10 | 1x | 0/0 | PO/IP | Tremor power ratio (0-60 minutes post harmaline) |
| 2 | Vehicle/ Harmaline | | | 0/30 | | |
| 3 | TA1(LSD)/ Harmaline | | | 100 ug/kg/30 | | Locomotor activity Harmaline brain concentration (Groups 2-4) |
| 4 | TA2(R-MDMA HCL)/Harmaline | | | 25 mg/kg/30 | | | to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

EXAMPLE 1

Experimental Procedures

This experiment was performed in rats (CD/SD), source Charles River Labs, age or weight: 180-200 grams on arrival, sex: male. Randomization: Animals were assigned randomly to treatment groups.

Route of administration for harmaline was IP, for TA was PO. Dose volume was 3 mL/kg. Formulation(s): harmaline: 0.9% saline; TA: PBS is used as a vehicle for TA. Dose Levels: harmaline: 30 mg/kg; LSD—100 ug/kg PO, Methods Male CD/SD rats (CRL) were used, 180-200 g at time of arrival. They were acclimated for 5-7 days prior to testing. Each rat was tested only once and then euthanized for brain tissue collection.

Drugs

Harmaline (harmaline HCl dihydrate; Sigma H1392-1) was obtained by Melior and formulated using a free-base correction factor of 1.33 in saline at 10 mg/mL (13.3 mg/mL with correction) and administered at 3 ml/kg by IP route.

Saline (0.9% NaCl) was formulated at Melior using sterile filtered water.

Testing Procedure

For groups 1-4 each animal received two treatments 15 minutes apart (see TABLE 1). The first treatment was either TA or vehicle. The second treatment was either harmaline or saline. Immediately after the second dosing, the animal was placed into the actimeter (BASi Force Plate Actimeter). The actimeter consists of an enclosed container (41.6×41.6 cm) containing a rigid plate that rests on four force transducers placed at each corner. The transducers measure the distribution of forces exerted by the animal while moving about.

Four treatment groups were evaluated in this study, with the test agent, dose levels, and N per group listed in TABLE 1. Motor activity was monitored for 60 minutes after administration of the second test agent (harmaline or saline). TPR was calculated as the average of the tremor during or a 10-minute period for six successive 10 minute periods beginning at 0 minutes after harmaline administration (i.e., from 0 minutes to 60 minutes).

Tremor power was evaluated using the ratio TPR=(P2)/(P1+P3), where Pn=integrated power over (1) 1.5-8 Hz, (2) 8-13 Hz, and (3) 13-25 Hz (the frequency range may be optimized depending on the actual data at the time of testing). The Tremor Power Ratios were evaluated by 3-factor ANOVA (Time, Frequency, Treatment)

As part of the analysis, brain levels of harmaline were measured. Outliers with low brain harmaline levels (greater than 2 standard deviations) were excluded from analysis.

Tissue Samples and Euthanasia

Brains were harvested from all animals treated with harmaline at 60 minutes (end of testing). The brains of those rats were removed, divided into two hemispheres along the mid-sagittal plane, weighed, and rapidly frozen on dry ice. The concentrations of harmaline were evaluated by HPLC-mass spectroscopy in the left hemispheres.

Results and Discussion

The harmaline-induced model is a classical animal model of action tremor. (Pan, et al. Animal models of tremor: relevance to human tremor disorders. Tremor Other Hyperkinet Mov. 2018; 8.) A single dose of harmaline can induce action tremor by enhancing the coupling between the inferior olivary (IO) neurons. Harmaline-induced tremor is predominantly an action tremor that responds to propranolol, primidone, and alcohol. Therefore, harmaline-induced tremor has long been postulated to be an animal model of ET. Harmaline belongs to a group of naturally occurring compounds, called β-alkaloids. In ET patient blood and brain, increased harmaline-related β-alkaloids, such as harmane, have been observed, suggesting that environmental factors can contribute to oscillatory activities in the olivocerebellar system in ET patients. Harmaline has been shown to induce action tremor in a wide variety of animals, including mice, rats, cats, monkeys, and pigs, suggesting an evolutionarily conserved olivocerebellar circuit for tremor generation. Harmaline-induced tremor model has been tested in pre-clinical studies for ET for the development of a gap junction blocker, carbenoxolone, and a T-type calcium channel blocker. Translational validity of this model is confirmed in clinical studies. Therefore, results obtained in this model can predict clinical efficacy of tested compound in humans.

FIG. 1 shows an example of locomotor activity/movement data from the harmaline-induced tremor model in rats with Propranolol (15 mg/kg, IP) used as a positive control. Measurements were done every 10 minutes over 60 minutes post harmaline administration. 10 rats per group. *–P<0.05, **–P<0.01, 3-factor ANOVA (Time, Frequency, Treatment).

Figure 2:
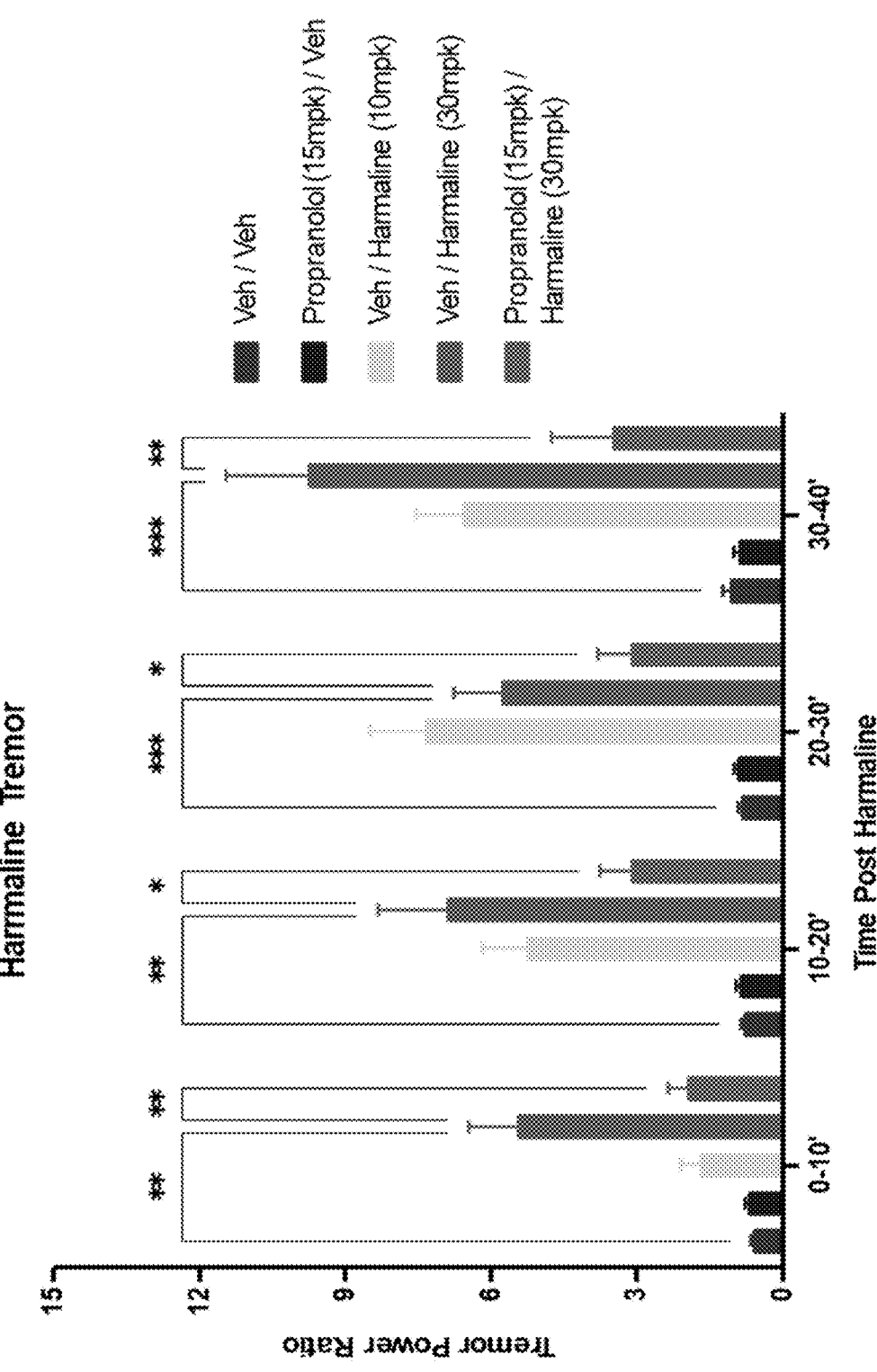
FIG. 2 is a graph of tremor power ratio data from a harmaline-induced tremor model in rats.

FIG. 2 shows an example of tremor power ratio data from the harmaline-induced tremor model in rats with Propranolol (15 mg/kg, IP) used as a positive control. Measurements were done every 10 minutes over 60 minutes post harmaline administration. 10 rats per group. *–P<0.05, –P<0.01, *–P<0.001 3-factor ANOVA (Time, Frequency, Treatment).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Handforth, A. Harmaline Tremor: Underlying Mechanisms in a Potential Animal Model of Essential Tremor. Tremor and Other Hyperkinetic Movements, pps. 1-14.
2. Kulkarni S K, Kaul P N. Modification by levo-propranolol of tremors induced by harmaline in mice. Experientia 1979: 35:1627-28.
3. Long M A, Deans M R, Paul D L, Connors B W. Rhythmicity without synchrony in the electrically uncoupled inferior olive. J Neurosci. 2002; 22:10898-905.
4. Martin F C, Thu Le A, Handforth A. Harmaline-induced tremor as a potential preclinical screening method for essential tremor medications. Mov Disord. 2005; 20(3): 298-305.
5. Paul V. Involvement of beta 2-adrenoceptor blockade and 5-hydroxytryptamine mechanism in inhibition of harmaline-induced tremors in rats. Eur J Pharmacol. 1986; 122:111-5.
6. Sinton C M (1), Krosser B I, Walton K D, Llinás R R. The effectiveness of different isomers of octanol as blockers of harmaline-induced tremor. Pflugers Arch. 1989; 414:3

What is claimed is:

1. A method of treating Essential Tremor, comprising administering to an individual lysergic acid diethylamide (LSD) at a dose of 10-1000 μg or a pharmaceutically acceptable salt, solvate, isomer, or deuterated form thereof.

2. The method of claim 1, wherein the administration of LSD reduces undesired movement or tremors.

3. The method of claim 1, wherein the administration of LSD eliminates undesired movement or tremors.

4. The method of claim 1, wherein LSD is administered as a single dose.

5. The method of claim 1, wherein the Essential Tremor is an action tremor.

6. The method of claim 1, wherein the individual is administered a salt of LSD.

7. The method of claim 1, wherein the individual is administered LSD tartrate.

\* \* \* \* \*